(12) United States Patent
Simpson et al.

(10) Patent No.: US 7,708,749 B2
(45) Date of Patent: May 4, 2010

(54) DEBULKING CATHETERS AND METHODS

(75) Inventors: John B. Simpson, Woodside, CA (US); Himanshu Patel, San Jose, CA (US); Greg Stine, Longview, TX (US); Brett Follmer, Santa Clara, CA (US); Michael H. Rosenthal, San Carlos, CA (US); Mehrdad Farhangnia, Sunnyvale, CA (US)

(73) Assignee: Fox Hollow Technologies, Inc., Plymouth, MN (US)

( * ) Notice: Subject to any disclaimer, the term of this patent is extended or adjusted under 35 U.S.C. 154(b) by 1469 days.

(21) Appl. No.: 11/012,876

(22) Filed: Dec. 14, 2004

(65) Prior Publication Data

US 2005/0222663 A1   Oct. 6, 2005

Related U.S. Application Data

(63) Continuation-in-part of application No. 10/288,582, filed on Nov. 4, 2002, now abandoned, and a continuation-in-part of application No. 10/027,418, filed on Dec. 19, 2001.

(60) Provisional application No. 60/381,632, filed on May 17, 2002, provisional application No. 60/272,273, filed on Feb. 27, 2001, provisional application No. 60/257,704, filed on Dec. 20, 2000.

(51) Int. Cl.
*A61B 17/22* (2006.01)
*A61D 1/02* (2006.01)

(52) U.S. Cl. .................................. 606/159

(58) Field of Classification Search ............... None
See application file for complete search history.

(56) References Cited

U.S. PATENT DOCUMENTS

2,178,790 A    11/1939   Henry (Continued)

FOREIGN PATENT DOCUMENTS

DE    93 03 531 U1    7/1994

(Continued)

OTHER PUBLICATIONS

Brezinski et al., "Optical Coherence Tomography for Optical Biopsy," Circulation, 93:1206-1213 (1996).

(Continued)

*Primary Examiner*—Todd E Manahan
*Assistant Examiner*—Kevin Everage
(74) *Attorney, Agent, or Firm*—Popovich, Wiles & O'Connell, P.A.

(57) ABSTRACT

A method of removing material from a blood flow lumen includes providing a device having a cutting element and an opening, the cutting element being movable relative to the opening. The method then includes advancing the device through a patient's vascular system to the blood flow lumen. Finally, the method involves moving the cutting element and the opening relative to the blood flow lumen so that a continuous piece of material is severed by the cutting element and directed into the opening as the cutting element and opening move through the blood flow lumen, the continuous piece of severed material being directed into the device for removal from the patient. The method may include providing a device having a rotatable cutter that, in some embodiments, is not parallel to the longitudinal axis of the device, is movable, has retracted and deployed positions, or any combination thereof. The method may further include forcing the opening toward the wall of the vascular site after the advancing step and before the moving step.

34 Claims, 33 Drawing Sheets

U.S. PATENT DOCUMENTS

| | | |
|---|---|---|
| 3,705,577 A | 12/1972 | Sierra |
| 3,815,604 A | 6/1974 | O'Malley et al. |
| 3,831,585 A | 8/1974 | Brondy et al. |
| 3,837,345 A | 9/1974 | Matar |
| 3,995,619 A | 12/1976 | Glatzer |
| 4,210,146 A | 7/1980 | Banko |
| 4,669,469 A | 6/1987 | Gifford, III et al. |
| 4,696,298 A | 9/1987 | Higgins et al. |
| 4,771,774 A | 9/1988 | Simpson et al. |
| 4,781,186 A | 11/1988 | Simpson et al. |
| 4,817,613 A | 4/1989 | Jaraczewski et al. |
| 4,819,635 A | 4/1989 | Shapiro |
| 4,850,957 A | 7/1989 | Summers |
| 4,886,061 A | 12/1989 | Fischell et al. |
| 4,926,858 A | 5/1990 | Gifford, III et al. |
| RE033,258 E | 7/1990 | Onik et al. |
| 4,966,604 A | 10/1990 | Reiss |
| 4,979,951 A | 12/1990 | Simpson |
| 4,986,807 A | 1/1991 | Farr |
| 4,994,067 A | 2/1991 | Summers |
| 5,000,185 A | 3/1991 | Yock |
| 5,024,234 A | 6/1991 | Leary et al. |
| 5,024,651 A | 6/1991 | Shiber |
| 5,047,040 A | 9/1991 | Simpson et al. |
| 5,053,044 A | 10/1991 | Mueller et al. |
| 5,054,492 A | 10/1991 | Scribner et al. |
| 5,071,425 A | 12/1991 | Gifford, III et al. |
| 5,084,010 A | 1/1992 | Plaia et al. |
| 5,085,662 A | 2/1992 | Willard |
| 5,087,265 A | 2/1992 | Summers |
| 5,092,873 A | 3/1992 | Simpson et al. |
| 5,114,399 A * | 5/1992 | Kovalcheck ................ 604/22 |
| 5,154,724 A | 10/1992 | Andrews |
| 5,181,920 A | 1/1993 | Mueller et al. |
| 5,217,474 A | 6/1993 | Zacca et al. |
| 5,222,966 A | 6/1993 | Perkins et al. |
| 5,224,488 A | 7/1993 | Neuffer |
| 5,224,949 A | 7/1993 | Gomringer et al. |
| 5,226,909 A | 7/1993 | Evans et al. |
| 5,226,910 A | 7/1993 | Kajiyama et al. |
| 5,242,460 A | 9/1993 | Klein et al. |
| 5,250,059 A * | 10/1993 | Andreas et al. ............. 606/159 |
| 5,250,065 A | 10/1993 | Clement et al. |
| 5,269,793 A | 12/1993 | Simpson |
| 5,282,484 A | 2/1994 | Reger |
| 5,285,795 A | 2/1994 | Ryan et al. |
| 5,312,425 A | 5/1994 | Evans et al. |
| 5,318,032 A | 6/1994 | Lonsbury et al. |
| 5,318,528 A | 6/1994 | Heaven et al. |
| 5,321,501 A | 6/1994 | Swanson et al. |
| 5,370,651 A | 12/1994 | Summers |
| 5,372,601 A | 12/1994 | Lary |
| 5,372,602 A | 12/1994 | Burke |
| 5,395,313 A | 3/1995 | Naves et al. |
| 5,403,334 A | 4/1995 | Evans et al. |
| 5,419,774 A | 5/1995 | Willard et al. |
| 5,429,136 A | 7/1995 | Milo et al. |
| 5,431,673 A | 7/1995 | Summers et al. |
| 5,441,510 A | 8/1995 | Simpson et al. |
| 5,459,570 A | 10/1995 | Swanson et al. |
| 5,470,415 A | 11/1995 | Perkins et al. |
| 5,485,042 A | 1/1996 | Burke |
| 5,491,524 A | 2/1996 | Hellmuth et al. |
| 5,505,210 A | 4/1996 | Clement |
| 5,507,292 A | 4/1996 | Jang et al. |
| 5,507,760 A | 4/1996 | Wynne et al. |
| 5,507,795 A | 4/1996 | Chiang et al. |
| 5,514,115 A | 5/1996 | Frantzen et al. |
| 5,527,325 A | 6/1996 | Conley et al. |
| 5,549,601 A | 8/1996 | McIntyre et al. |
| 5,569,277 A | 10/1996 | Evans et al. |
| 5,571,122 A | 11/1996 | Kelly et al. |
| 5,571,130 A | 11/1996 | Simpson et al. |
| 5,584,842 A | 12/1996 | Fogarty et al. |
| 5,620,447 A | 4/1997 | Smith et al. |
| 5,624,457 A | 4/1997 | Farley et al. |
| 5,626,562 A | 5/1997 | Castro |
| 5,632,754 A * | 5/1997 | Farley et al. ................ 606/159 |
| 5,634,464 A | 6/1997 | Jang et al. |
| 5,643,296 A | 7/1997 | Hundertmark et al. |
| 5,643,298 A | 7/1997 | Nordgren et al. |
| 5,665,098 A | 9/1997 | Kelly et al. |
| 5,669,920 A | 9/1997 | Conley et al. |
| 5,674,232 A | 10/1997 | Halliburton |
| 5,695,506 A | 12/1997 | Pike et al. |
| 5,700,687 A | 12/1997 | Finn |
| 5,709,698 A | 1/1998 | Adams et al. |
| 5,733,296 A | 3/1998 | Rogers et al. |
| 5,741,270 A | 4/1998 | Hansen et al. |
| 5,776,114 A | 7/1998 | Frantzen et al. |
| 5,816,923 A | 10/1998 | Milo et al. |
| 5,823,971 A | 10/1998 | Robinson et al. |
| 5,830,224 A | 11/1998 | Cohn et al. |
| 5,836,957 A | 11/1998 | Schulz et al. |
| 5,843,103 A | 12/1998 | Wulfman |
| 5,868,685 A | 2/1999 | Powell et al. |
| 5,868,767 A | 2/1999 | Farley et al. |
| 5,883,458 A | 3/1999 | Sumita et al. |
| 5,895,402 A | 4/1999 | Hundertmark et al. |
| 5,911,734 A | 6/1999 | Tsugita et al. |
| 5,916,210 A | 6/1999 | Winston |
| 5,938,671 A | 8/1999 | Katoh et al. |
| 5,941,869 A | 8/1999 | Patterson et al. |
| 5,948,184 A | 9/1999 | Frantzen et al. |
| 5,951,482 A | 9/1999 | Winston et al. |
| 5,954,745 A | 9/1999 | Gertler et al. |
| 5,968,064 A | 10/1999 | Selmon et al. |
| 5,989,281 A | 11/1999 | Barbut et al. |
| 6,010,449 A | 1/2000 | Selmon et al. |
| 6,013,072 A | 1/2000 | Winston et al. |
| 6,016,649 A | 1/2000 | Bock et al. |
| 6,022,362 A | 2/2000 | Lee et al. |
| 6,027,450 A | 2/2000 | Brown et al. |
| 6,027,514 A | 2/2000 | Stine et al. |
| 6,036,656 A | 3/2000 | Slater |
| 6,036,707 A | 3/2000 | Spaulding |
| 6,048,349 A | 4/2000 | Winston et al. |
| 6,063,093 A | 5/2000 | Winston et al. |
| 6,068,638 A | 5/2000 | Makower |
| 6,081,738 A | 6/2000 | Hinohara et al. |
| 6,099,542 A | 8/2000 | Cohn et al. |
| 6,106,515 A | 8/2000 | Winston et al. |
| 6,120,515 A | 9/2000 | Rogers et al. |
| 6,120,516 A | 9/2000 | Selmon et al. |
| 6,134,003 A | 10/2000 | Tearney et al. |
| 6,157,852 A | 12/2000 | Selmon et al. |
| 6,159,225 A | 12/2000 | Makower |
| 6,183,432 B1 | 2/2001 | Milo |
| 6,190,353 B1 | 2/2001 | Makower et al. |
| 6,191,862 B1 | 2/2001 | Swanson et al. |
| 6,193,676 B1 | 2/2001 | Winston et al. |
| 6,217,527 B1 | 4/2001 | Selmon et al. |
| 6,217,549 B1 | 4/2001 | Selmon et al. |
| 6,221,049 B1 | 4/2001 | Selmon et al. |
| 6,228,076 B1 | 5/2001 | Winston et al. |
| 6,231,546 B1 | 5/2001 | Milo et al. |
| 6,235,000 B1 | 5/2001 | Milo et al. |
| 6,241,667 B1 | 6/2001 | Vetter et al. |
| 6,241,744 B1 | 6/2001 | Imran et al. |
| 6,258,052 B1 | 7/2001 | Milo |
| 6,266,550 B1 | 7/2001 | Selmon et al. |
| 6,283,951 B1 | 9/2001 | Flaherty et al. |
| 6,283,983 B1 | 9/2001 | Makower et al. |
| 6,299,622 B1 | 10/2001 | Snow et al. |

| | | |
|---|---|---|
| 6,302,875 B1 | 10/2001 | Makower et al. |
| 6,330,884 B1 | 12/2001 | Kim |
| 6,355,005 B1 | 3/2002 | Powell et al. |
| 6,375,615 B1 | 4/2002 | Flaherty et al. |
| 6,394,976 B1 | 5/2002 | Winston et al. |
| 6,398,798 B2 | 6/2002 | Selmon et al. |
| 6,428,552 B1 | 8/2002 | Sparks |
| 6,443,966 B1 | 9/2002 | Shiu |
| 6,445,939 B1 | 9/2002 | Swanson et al. |
| 6,447,525 B2 | 9/2002 | Follmer et al. |
| 6,475,226 B1 | 11/2002 | Belef et al. |
| 6,623,496 B2 | 9/2003 | Snow et al. |
| 6,638,233 B2 | 10/2003 | Corvi et al. |
| 6,997,934 B2 | 2/2006 | Snow et al. |
| 7,318,831 B2 | 1/2008 | Alvarez et al. |
| 2002/0022788 A1 | 2/2002 | Corvi et al. |
| 2002/0077642 A1 | 6/2002 | Patel et al. |
| 2003/0018346 A1 | 1/2003 | Follmer et al. |
| 2003/0120295 A1 | 6/2003 | Simpson et al. |
| 2003/0125757 A1 | 7/2003 | Patel et al. |
| 2003/0125758 A1 | 7/2003 | Simpson et al. |
| 2004/0167553 A1 | 8/2004 | Simpson et al. |
| 2004/0167554 A1 | 8/2004 | Simpson et al. |
| 2007/0010840 A1 | 1/2007 | Rosenthal et al. |
| 2007/0276419 A1 | 11/2007 | Rosenthal |

FOREIGN PATENT DOCUMENTS

| | | |
|---|---|---|
| DE | 44 44 166 A1 | 6/1996 |
| WO | WO 02/45598 A2 | 6/2002 |

OTHER PUBLICATIONS

Brezinski et al., "Assessing Atherosclerotic Plaque Morphology: Comparison of Optical Coherence Tomography and High Frequency Intravascular Ultrasound," Heart, 77:397-403 (1997).

Huang et al., "Optical Coherence Tomography," Science, 254:1178-1181 (1991).

International Search Report and Written Opinion of PCT Application No. PCT/US04/12600, dated Jun. 13, 2008, 8 pages total.

International Search Report of PCT Application No. PCT/US04/12601, dated Jun. 30, 2005, 3 pages total.

U.S. Appl. No. 10/288,559, filed Nov. 4, 2002, Himanshu Patel et al. (59 pages).

U.S. Appl. No. 10/421,980, filed Apr. 22, 2003, John B. Simpson et al. (36 pages).

U.S. Appl. No. 10/288,582, filed Nov. 4, 2002, John B. Simpson et al. (48 pages).

U.S. Appl. No. 12/431,210, filed Apr. 28, 2009, John B. Simpson et al. (59 pages).

Abstract of DE 44 44 166 A1 (1 page).

Mar. 27, 2009 Communication from the European Patent Office regarding corresponding EP Application No. 01 991 343.3 (7 pages).

* cited by examiner

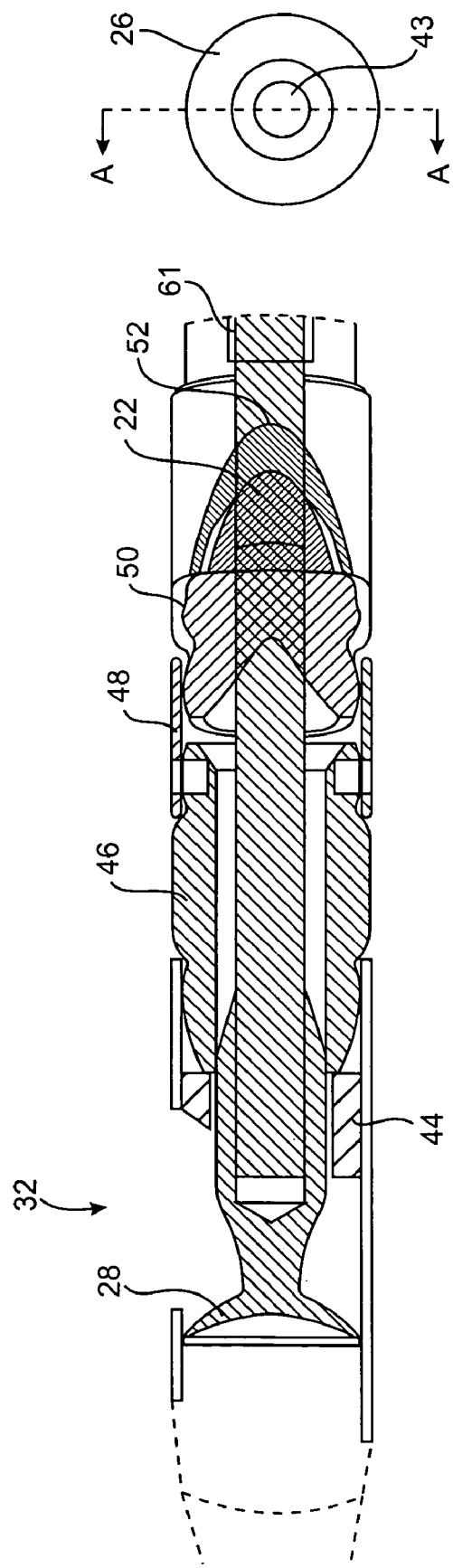

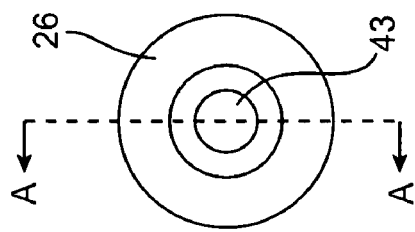
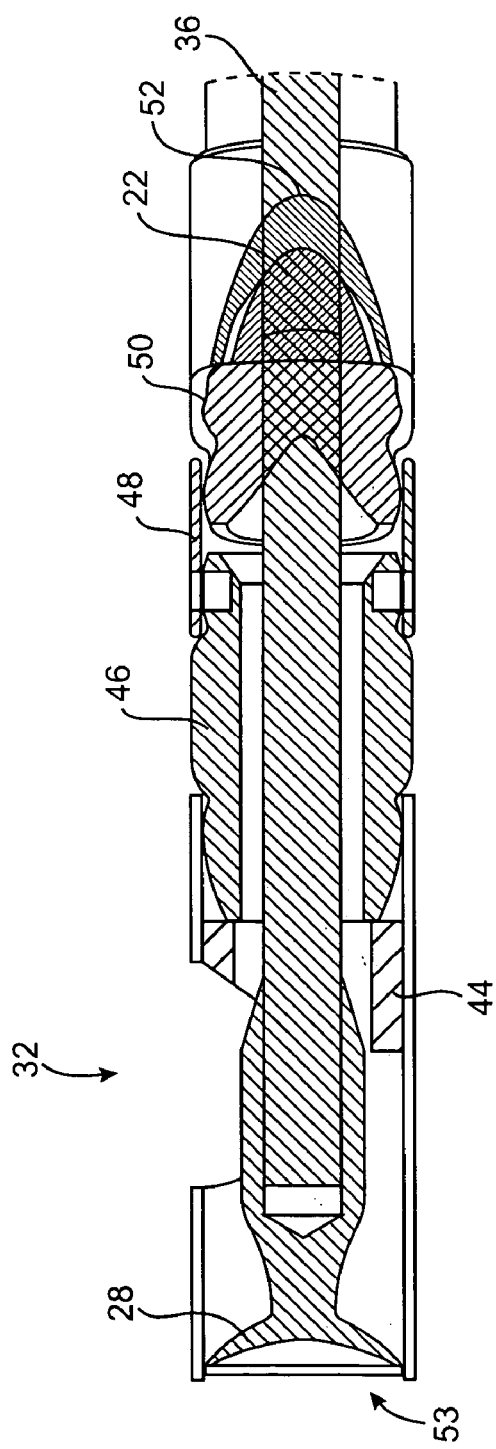

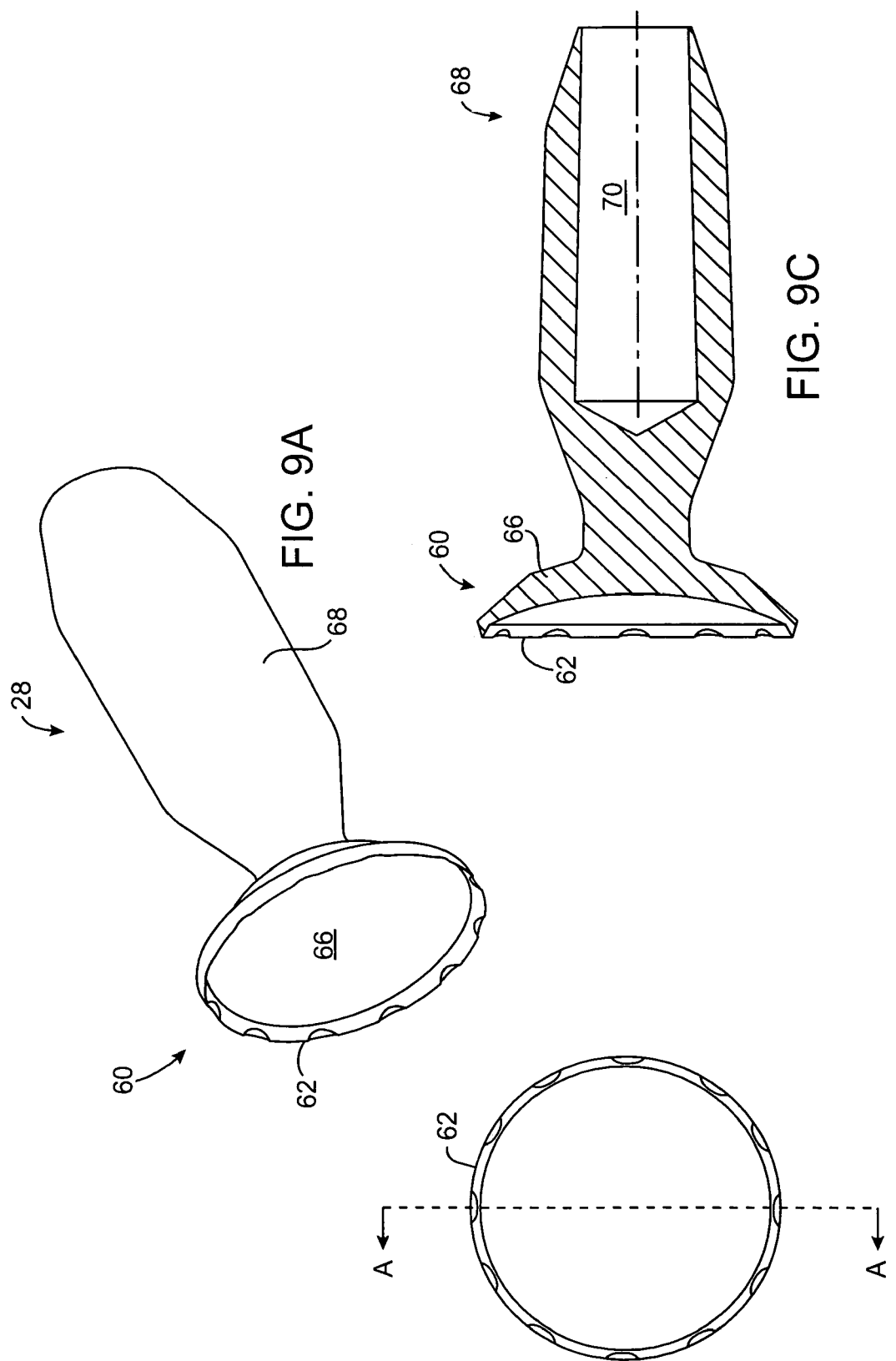

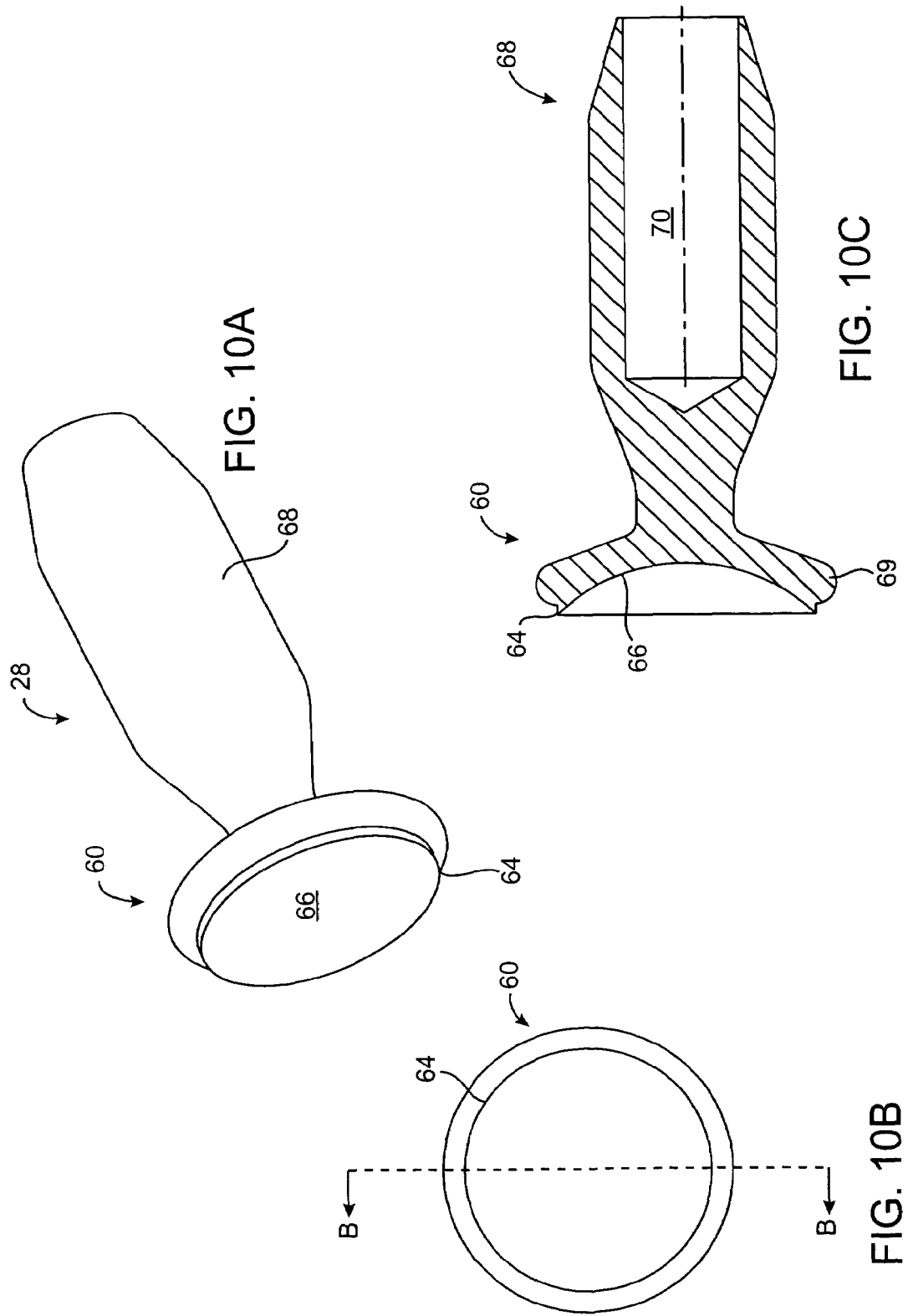

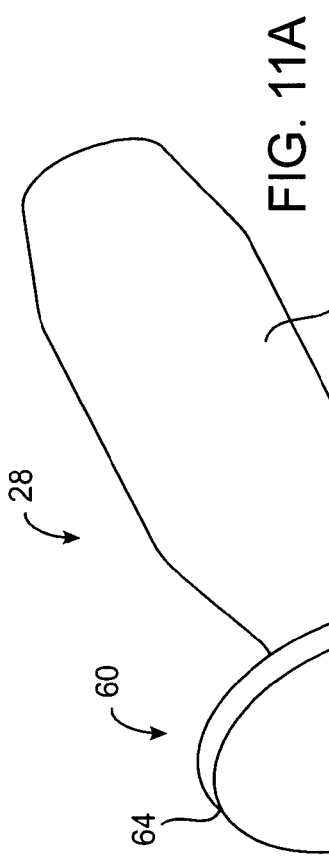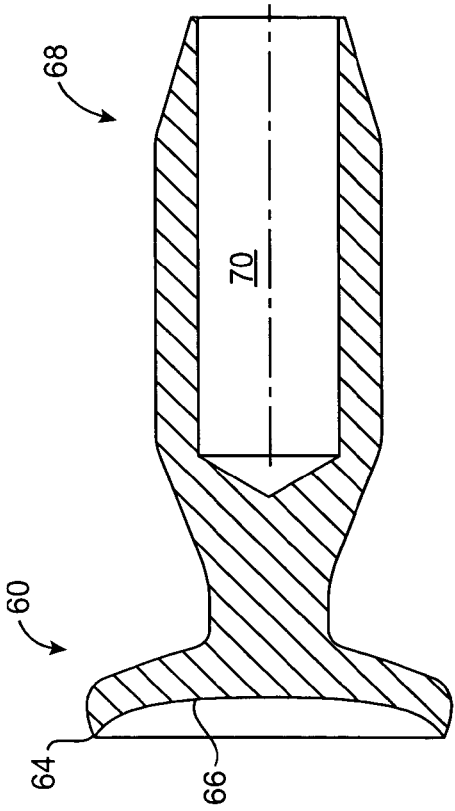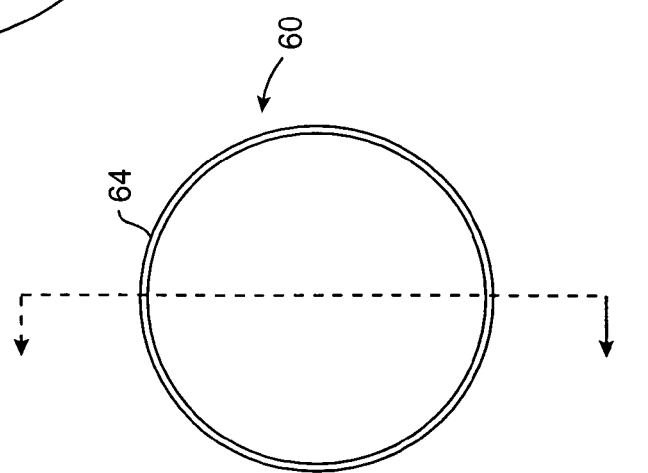

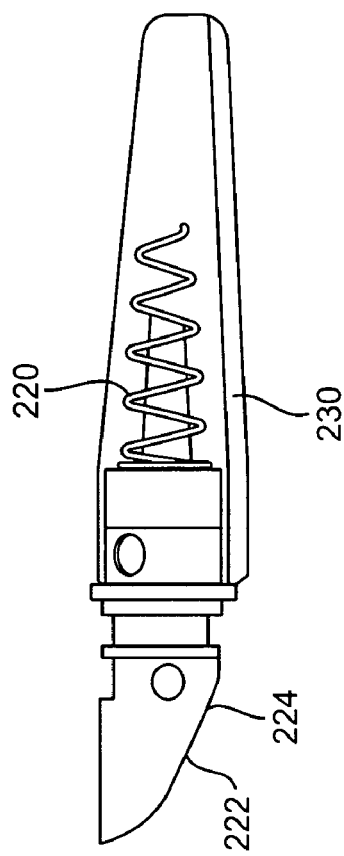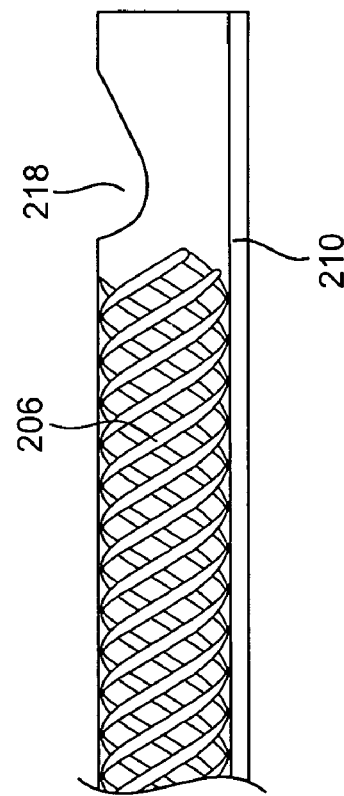
FIG. 25

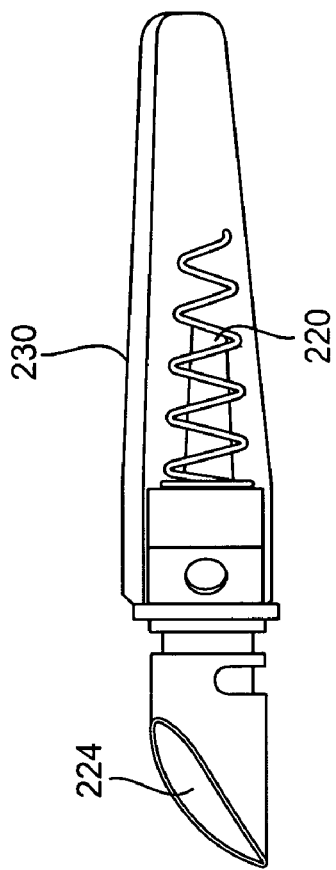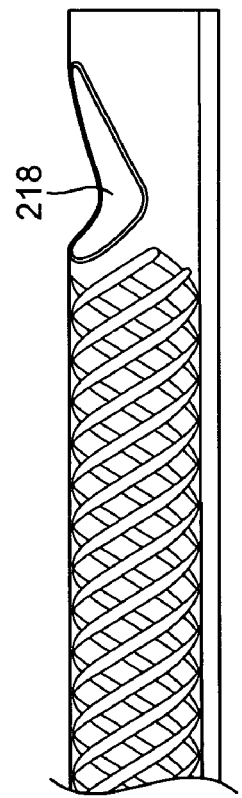
FIG. 27

DEBULKING CATHETERS AND METHODS

CROSS-REFERENCES TO RELATED APPLICATIONS

The present application is a continuation-in-part of U.S. patent application Ser. No. 10/288,582, filed Nov. 4, 2002, now abandoned entitled "Debulking Catheters and Methods" which claims the benefit of Provisional Application No. 60/381,632, filed on May 17, 2002, entitled "Debulking Catheter" and which is also a continuation-in-part of U.S. patent application Ser. No. 10/027,418, filed Dec. 19, 2001, entitled "Debulking Catheter", which claims the benefit of Provisional Patent Application Ser. No. 60/257,704, filed Dec. 20, 2000, entitled "Debulking Catheter" and Provisional Patent Application Ser. No. 60/272,273 filed Feb. 27, 2001, entitled "Debulking Catheter", the complete disclosures of which are incorporated herein by reference.

The present application is also related to U.S. patent application Ser. No. 09/377,884, filed Aug. 19, 1999, entitled "Apparatus and Methods for Material Capture and Removal" and Ser. No. 09/377,894, filed Aug. 19, 1999, entitled "Apparatus and Methods for Removing Material From a Body Lumen," the complete disclosures of which are incorporated by reference.

BACKGROUND OF THE INVENTION

The present invention relates generally to systems and methods for debulking body lumens. More particularly, the present invention relates to atherectomy catheters for excising atheroma and other materials from blood vessels and from stents.

Cardiovascular disease frequently arises from the accumulation of atheromatous material on the inner walls of vascular lumens, particularly arterial lumens of the coronary and other vasculature, resulting in a condition known as atherosclerosis. Atherosclerosis occurs naturally as a result of aging, but may also be aggravated by factors such as diet, hypertension, heredity, vascular injury, and the like. Atheromatous and other vascular deposits restrict blood flow and can cause ischemia which, in acute cases, can result in myocardial infarction. Atheromatous deposits can have widely varying properties, with some deposits being relatively soft and others being fibrous and/or calcified. In the latter case, the deposits are frequently referred to as plaque.

One conventional treatment for cardiovascular disease is the use of stents. Endoluminal stents are commonly used to treat obstructed or weakened body lumens, such as blood vessels and other vascular lumens. Once deployed in the blood vessel, the stent can remain in the body lumen where it will maintain the patency of the lumen and/or support the walls of the lumen which surround it. One factor impeding the success of stent technology in endoluminal treatments is the frequent occurrence of in-stent restenosis, characterized by proliferation and migration of smooth muscle cells within and/or adjacent to the implanted stent, causing reclosure or blockage of the body lumen.

Atherosclerosis and restenosis can be treated in a variety of ways, including drugs, bypass surgery, and a variety of catheter-based approaches which rely on intravascular debulking or removal of the atheromatous or other material occluding a blood vessel. Of particular interest to the present invention, a variety of methods for cutting or dislodging material and removing such material from the blood vessel have been proposed, generally being referred to as atherectomy procedures. Atherectomy catheters intended to excise material from the blood vessel lumen generally employ a rotatable and/or axially translatable cutting blade which can be advanced into or past the occlusive material in order to cut and separate such material from the blood vessel lumen. In particular, side-cutting atherectomy catheters generally employ a housing having an aperture on one side, a blade which is rotated or translated by the aperture, and a balloon to urge the aperture against the material to be removed.

Although atherectomy catheters have proven very successful in treating many types of atherosclerosis and in-stent restenosis, improved atherectomy catheters and methods are continuously being pursued. For example, many currently available side-cutting atherectomy catheters have difficulty in capturing occluding material in the cutting aperture. To facilitate material capture, the cutting aperture is frequently elongated to increase the area into which the material can penetrate. Such elongation typically requires an equivalent lengthening of the cutter housing. Since most cutter housings are rigid, such lengthening makes it more difficult to introduce the distal end of the catheter through tortuous regions of the vasculature.

Another shortcoming of many currently available atherectomy catheters is that they typically require a balloon positioned opposite the cutting window to urge the cutting window into contact with occluding material. Such balloons, however, unduly increase the size of the distal portion of the catheter. Even with the balloon, the amount of material that can be removed by conventional atherectomy catheters is limited by the size of the cutting window. Other disadvantages of some catheters include cutting elements with less than ideal hardness, inadequate storage space within the catheter for containing removed material, sub-optimal guide wire lumens, and/or the like.

For these reasons, it would be advantageous to have atherectomy catheters, and methods for their use, which could access small, tortuous regions of the vasculature and remove atheromatous and other occluding materials from within blood vessels and stents in a controlled fashion. In particular, it would be desirable to have atherectomy catheters and methods which could facilitate capturing and invagination of atheromatous materials. Ideally, such catheters and methods would be adaptable for use in a variety of body lumens, including but not limited to coronary and other arteries. At least some of these objectives will be met by the present invention.

The present invention also relates to methods and devices for removing tissue from a body lumen such as a blood vessel or other vascular location. In particular, the present invention may be used for removing material from a vascular location but may find uses in other body lumens as well. It is understood that although the invention may be described with respect to use in blood vessels the methods and devices of the present invention may be practiced in any body lumen.

The present invention also relates to methods and devices for removing tissue from an atherectomy device and for storing material which has been removed from the atherectomy device.

BRIEF SUMMARY OF THE INVENTION

The present invention provides catheters and methods for removing material from (or "debullking") a body lumen. Catheters of the present invention may be used in a variety of body lumens, including but not limited to intravascular lumens such as coronary arteries. Typically, debulking catheters are used to remove occlusive material, such as atherosclerotic plaque, from vascular lumens, but they may alternatively be used to remove other materials. Generally, debulking catheters include a proximal portion, a distal portion having an opening (or "window"), and a cutting element (or "tissue debulking assembly") which may be exposed through the opening to contact material in a body lumen. The catheter debulks a body lumen when it is moved while the cutting element is in contact with the material in the lumen.

In one aspect of the present invention, a method of removing material from a blood flow lumen includes: providing a device having a cutting element and an opening, the cutting element being movable relative to the opening; advancing the device through a patient's vascular system to the blood flow lumen; and moving the cutting element and the opening relative to the blood flow lumen so that a continuous piece of material is severed by the cutting element and directed into the opening as the cutting element and opening move through the blood flow lumen, the continuous piece of severed material being directed into the device for removal from the patient. In some embodiments, the providing step is carried out with the cutting element being movable between a deployed position and a retracted position, the cutting element extending out of the opening when in the deployed position and not extending out of the opening when in the retracted position. In such embodiments, the advancing step is typically carried out with the cutting element being in the retracted position, and the moving step is typically carried out with the cutting element being in the deployed position.

In some embodiments, the providing step is carried out with the cutting element extending beyond the opening a distance of about 0.025 mm to about 0.64 mm. In other embodiments, the providing step is carried out with the cutting element being rotatable, and with the moving step being carried out with the cutting element rotating when severing the material. In some embodiments, for examples, the providing step is carried out with the device having a longitudinal axis, and the moving step is carried out with the cutting element rotating around an axis which is not parallel to the longitudinal axis of the device. In other embodiments, the providing step is carried out with an axis around which the cutting element rotates being movable relative to the opening.

In some embodiments, the moving step is carried out by moving the cutting element and window in a distal direction. Optionally, in such embodiments the moving step may be carried out with the material being contained in the device at a location distal to the cutting element.

Other embodiments may further include the step of forcing the opening toward the wall of the vascular site after the advancing step and before the moving step. In such embodiments, the forcing step may be carried out by bending the device so that the opening is forced against the wall of the vascular site. Optionally, the providing step may be carried out with the opening being on a side of the device, the forcing step may be carried out to force the side against the blood flow lumen, and the moving step may be carried out with the cutting element extending out of the opening, the cutting element directing the continuous piece of material into the opening.

The present invention is also directed to an atherectomy device which has a second opening in the body which is selectively closed or opened by a user. The second opening is closed when the cutting element is used to cut material from the vascular location and is opened when removing material from the containment chamber. The guidewire may be used to keep the second opening closed while the guidewire is positioned in the guidewire lumen. The material may be forced through either the second opening or the first or working opening through which the material enters the device. The material may be forced through one of the openings using any suitable medium or device such as a fluid, a pusher element or the cutting element.

In another aspect of the present invention, the device may include two or more detachable containment chambers. By providing more than one detachable containment chamber the user may replace one of the chambers while the other chamber is being cleaned.

For a further understanding of the nature and advantages of the invention, reference should be made to the following description taken in conjunction with the accompanying drawings.

BRIEF DESCRIPTION OF THE DRAWINGS

FIG. 3A is an end view of the distal portion of the debulking catheter of FIG. 1 in which the cutter is in a closed position in the catheter body;

FIG. 3B is a sectional view along Line A-A of FIG. 3A;

FIG. 5A is an end view of the distal portion of the debulking catheter of FIG. 1 in which the cutter is in a packing position within a tip of the catheter;

FIG. 5B is a sectional view along Line A-A of FIG. 5A;

FIG. 9A is a perspective view of a cutter of the present invention;

FIG. 9B is an end view of the cutter of FIG. 9A;

FIG. 9C is a sectional view of the cutter along Line A-A of the cutter of FIGS. 9A and 9B;

FIG. 10A is a perspective view of an in-stent restenosis cutter of the present invention;

FIG. 10B is an end view of the cutter of FIG. 10A;

FIG. 10C is a sectional view of the cutter along Line B-B of the cutter of FIGS. 10A and 10B;

FIG. 11A is a perspective view of another in-stent restenosis cutter of the present invention;

FIG. 11B is an end view of the cutter of FIG. 11A;

FIG. 11C is a sectional view of the cutter along Line C-C of the cutter of FIGS. 11A and 11B;

FIG. 25 is an exploded view of FIG. 24.

FIG. 27 is an exploded view of FIG. 26.

DETAILED DESCRIPTION OF THE INVENTION

Figure 1:
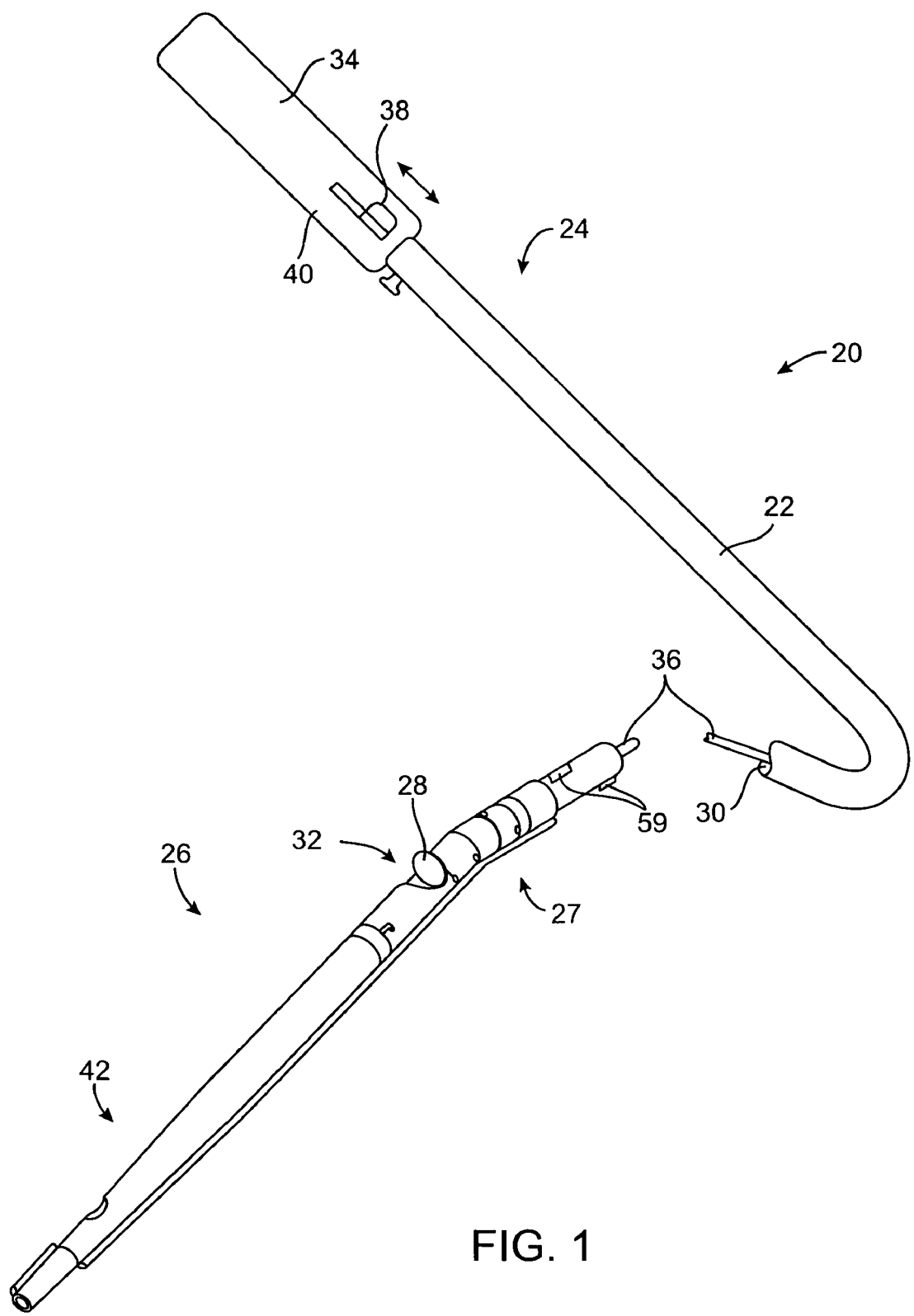
FIG. 1 is a perspective view of a debulking catheter of the present invention.

The catheters and methods of the present invention are designed to debulk atheroma and other occlusive material from diseased body lumens, and in particular coronary arteries, de novo lesions, and in-stent restenosis lesions. The catheters and methods, however, are also suitable for treating stenoses of body lumens and other hyperplastic and neoplastic conditions in other body lumens, such as the ureter, the biliary duct, respiratory passages, the pancreatic duct, the lymphatic duct, and the like. Neoplastic cell growth will often occur as a result of a tumor surrounding and intruding into a body lumen. Debulking of such material can thus be beneficial to maintain patency of the body lumen. While the remaining discussion is directed at debulking and passing through atheromatous or thrombotic occlusive material in a coronary artery, it will be appreciated that the systems and methods of the present invention can be used to remove and/or pass through a variety of occlusive, stenotic, or hyperplastic material in a variety of body lumens.

Apparatus according to the present invention will generally comprise catheters having catheter bodies adapted for intraluminal introduction to the target body lumen. The dimensions and other physical characteristics of the catheter bodies will vary significantly depending on the body lumen which is to be accessed. In the exemplary case of atherectomy catheters intended for intravascular introduction, the proximal portions of the catheter bodies will typically be very flexible and suitable for introduction over a guidewire to a target site within the vasculature. In particular, catheters can be intended for "over-the-wire" introduction when a guidewire channel extends fully through the catheter body or for "rapid exchange" introduction where the guidewire channel extends only through a distal portion of the catheter body. In other cases, it may be possible to provide a fixed or integral coil tip or guidewire tip on the distal portion of the catheter or even dispense with the guidewire entirely. For convenience of illustration, guidewires will not be shown in all embodiments, but it should be appreciated that they can be incorporated into any of these embodiments.

Catheter bodies intended for intravascular introduction will typically have a length in the range from 50 cm to 200 cm and an outer diameter in the range from 1 French to 12 French (0.33 mm: 1 French), usually from 3 French to 9 French. In the case of coronary catheters, the length is typically in the range from 125 cm to 200 cm, the diameter is preferably below 8 French, more preferably below 7 French, and most preferably in the range from 2 French to 7 French. Catheter bodies will typically be composed of an organic polymer which is fabricated by conventional extrusion techniques. Suitable polymers include polyvinylchloride, polyurethanes, polyesters, polytetrafluoroethylenes (PTFE), silicone rubbers, natural rubbers, and the like. Optionally, the catheter body may be reinforced with braid, helical wires, coils, axial filaments, or the like, in order to increase rotational strength, column strength, toughness, pushability, and the like. Suitable catheter bodies may be formed by extrusion, with one or more channels being provided when desired. The catheter diameter can be modified by heat expansion and shrinkage using conventional techniques. The resulting catheters will thus be suitable for introduction to the vascular system, often the coronary arteries, by conventional techniques.

The distal portion of the catheters of the present invention may have a wide variety of forms and structures. In many embodiments, a distal portion of the catheter is more rigid than a proximal portion, but in other embodiments the distal portion may be equally as flexible as the proximal portion. One aspect of the present invention provides catheters having a distal portion with a reduced rigid length. The reduced rigid length can allow the catheters to access and treat tortuous vessels and small diameter body lumens. In most embodiments a rigid distal portion or housing of the catheter body will have a diameter that generally matches the proximal portion of the catheter body, however, in other embodiments, the distal portion may be larger or smaller than the flexible portion of the catheter.

A rigid distal portion of a catheter body can be formed from materials which are rigid or which have very low flexibilities, such as metals, hard plastics, composite materials, NiTi, steel with a coating such as titanium nitride, tantalum, ME-92®, diamonds, or the like. Most usually, the distal end of the catheter body will be formed from stainless steel or platinum/iridium. The length of the rigid distal portion may vary widely, typically being in the range from 5 mm to 35 mm, more usually from 10 mm to 25 mm, and preferably between 6 mm and 8 mm. In contrast, conventional catheters typically have rigid lengths of approximately 16 mm.

The side opening windows of the present invention will typically have a length of approximately 2 mm. In other embodiments, however, the side opening cutting window can be larger or smaller, but should be large enough to allow the cutter to protrude a predetermined distance that is sufficient to debulk material from the body lumen.

The catheters of the present invention can include a flexible atraumatic distal tip coupled to the rigid distal portion of the catheter. For example, an integrated distal tip can increase the safety of the catheter by eliminating the joint between the distal tip and the catheter body. The integral tip can provide a smoother inner diameter for ease of tissue movement into a collection chamber in the tip. During manufacturing, the transition from the housing to the flexible distal tip can be finished with a polymer laminate over the material housing. No weld, crimp, or screw joint is usually required.

The atraumatic distal tip permits advancing the catheter distally through the blood vessel or other body lumen while reducing any damage caused to the body lumen by the catheter. Typically, the distal tip will have a guidewire channel to permit the catheter to be guided to the target lesion over a guidewire. In some exemplary configurations, the atraumatic distal tip comprises a coil. In some configurations the distal tip has a rounded, blunt distal end. The catheter body can be tubular and have a forward-facing circular aperture which communicates with the atraumatic tip. A collection chamber can be housed within the distal tip to store material removed from the body lumen. The combination of the rigid distal end and the flexible distal tip is approximately 30 mm.

A rotatable cutter or other tissue debulking assembly may be disposed in the distal portion of the catheter to sever material which is adjacent to or received within the cutting window. In an exemplary embodiment, the cutter is movably disposed in the distal portion of the catheter body and movable across a side opening window. A straight or serrated cutting blade or other element can be formed integrally along a distal or proximal edge of the cutting window to assist in severing material from the body lumen. In one particular embodiment, the cutter has a diameter of approximately 1.14 mm. It should be appreciated however, that the diameter of the cutter will depend primarily on the diameter of the distal portion of the catheter body.

In exemplary embodiments, activation of an input device can deflect a distal portion of the catheter relative to the proximal portion of the catheter. Angular deflection of the distal portion may serve one or more purposes in various embodiments. Generally, for example, deflection of the distal portion increases the effective "diameter" of the catheter and causes the debulking assembly to be urged against material in a lumen, such as atherosclerotic plaque. In other embodiments, deflection of the distal portion may act to expose a debulking assembly through a window for contacting material in a lumen. In some embodiments, for example, activation of the input device moves the debulking assembly over a ramp or cam so that a portion of the rigid distal portion and flexible tip are caused to drop out of the path of the debulking assembly so as to expose the debulking assembly through the window. In some embodiments, deflection may both urge a portion of the catheter into material in a lumen and expose a tissue debulking assembly.

Some embodiments further help to urge the debulking assembly into contact with target tissue by including a proximal portion of the catheter body having a rigid, shaped or deformable portion. For example, some embodiments include a proximal portion with a bend that urges the debulking assembly toward a side of the lumen to be debulked. In other embodiments, one side of the proximal portion is less rigid than the other side. Thus, when tension is placed on the catheter in a proximal direction (as when pulling the debulking assembly proximally for use), one side of the proximal portion collapses more than the other, causing the catheter body to bend and the debulking assembly to move toward a side of the lumen to be debulked.

In exemplary embodiments, the debulking assembly comprises a rotatable cutter that is movable outside the window. By moving the cutter outside of the cutting window beyond an outer diameter of the distal portion of the catheter, the cutter is able to contact and sever material that does not invaginate the cutting window. In a specific configuration, the rotating cutter can be moved over the cam within the rigid, or distal, portion of the catheter body so that the cutting edge is moved out of the window. Moving the rotating cutter outside of the cutting window and advancing the entire catheter body distally, a large amount of occlusive material can be removed. Consequently, the amount of material that can be removed is not limited by the size of the cutting window.

As will be described in detail below, in some situations it is preferable to provide a serrated cutting edge, while in other situations it may be preferable to provide a smooth cutting edge. Optionally, the cutting edge of either or both the blades may be hardened, e.g., by application of a coating. A preferred coating material is a chromium based material, available from ME-92, Inc., which may be applied according to manufacturer's instructions. In some embodiments, the cutter includes a tungsten carbide cutting edge. Other rotatable and axially movable cutting blades are described in U.S. Pat. Nos. 5,674,232; 5,242,460; 5,312,425; 5,431,673; and 4,771,774, the full disclosures of which are incorporated herein by reference. In some embodiments, a rotatable cutter includes a beveled edge for removal of material from a body lumen while preventing injury to the lumen. In still other embodiments, a tissue debulking assembly may include alternative or additional features for debulking a lumen. For example, the debulking assembly may include, but is not limited to, a radio frequency device, an abrasion device, a laser cutter and/or the like.

The catheters of the present invention may include a monorail delivery system to assist in positioning the cutter at the target site. For example, the tip of the catheter can include lumen(s) that are sized to receive a conventional guidewire (typically 0.014" diameter) or any other suitable guidewire (e.g., having diameters between 0.018" and 0.032") and the flexible proximal portion of the catheter body can include a short lumen (e.g., about 12 centimeters in length). Such a configuration moves the guidewire out of the rigid portion so as to not interfere with the debulking assembly.

In other embodiments, however, the guidewire lumen may be disposed within or outside the flexible proximal portion of the catheter body and run a longer or shorter length, and in fact may run the entire length of the flexible portion of the catheter body. The guidewire can be disposed within lumen on the flexible portion of the catheter body and exit the lumen at a point proximal to the rigid portion of the catheter. The guidewire can then enter a proximal opening in the tip lumen and exit a distal opening in the tip lumen. In some embodiments, the catheter has a distal guidewire lumen on its flexible distal tip and a proximal guidewire lumen on its flexible body. For example, in some embodiments the distal lumen may have a length of between about 2.0 cm and about 3.0 cm and the proximal lumen may have a length of between about 10 cm and about 14 cm. In yet further embodiments, a distal tip guidewire lumen may be configured to telescope within a proximal guidewire lumen, or vice versa. A telescoping guidewire lumen may enhance performance of the catheter by preventing a guidewire from being exposed within a body lumen.

The present invention may optionally employ any of a wide variety of conventional radiopaque markers, imaging devices, and/or transducers. In exemplary embodiments, the catheters of the present invention can include a radiopaque distal portion and/or radiopaque markers disposed on a distal portion of the catheter body, such as proximal and distal of the cutting window, on the cam or ramp, so as to allow the user to track the position of the cutter, or the like. The catheters of the present invention will also be particularly useful with ultrasonic transducers, such as an IVUS, of a type which may be deployed linearly within the catheter body or circumferentially on the debulking assembly. Linear deployment will allow viewing along a discrete length of the catheter axis, preferably adjacent to the cutting point, usually over a length in the range from 1 mm to 30 mm, preferably 2 mm to 10 mm. Circumferentially deployed phased arrays may subtend a viewing arc in the range from 5° to 360°, usually from 180° to 360°. For imaging transducers located on cutting blades within a housing or second cutting element, the field of imaging will generally be limited by the dimensions of the aperture. In some cases, however, it might be possible to fabricate all or a portion of the cutter blade/housing out of an ultrasonically translucent material. A more complete description of suitable imaging catheters are described more fully in U.S. patent application Ser. No. 09/378,224, filed Aug. 19, 1999, and entitled "Atherectomy Catheter with Aligned Imager," now U.S. Pat. No. 6,299,622 B1, the complete disclosure of which is incorporated herein by reference. In addition to ultrasonic array transducers, the imaging devices of the present invention may comprise optical coherence tomography devices, such as described in U.S. Pat. No. 5,491,524, the full disclosure of which is incorporated herein by reference, as well as Huang et al. (1991) Science 254:1178-1181; Brezinski et al. (1997) Heart 77:397-403; and Brezinski et al (1996) Circulation 93:1206-1213. In some instances, the present invention may also provide optical imaging using optical wave guides and the like.

Referring now to FIG. 1, a catheter 20 constructed in accordance with principles of the present invention comprises a catheter body 22 having a proximal portion 24 and a distal portion 26. Proximal portion 24 can be coupled to distal portion 26 with a connection assembly 27 to allow pivoting or deflection of distal portion 26 relative to proximal portion 24. A proximal end of the catheter body 22 can have a handle 40 for manipulation by a user, a luer for connection to an aspiration or fluid delivery channel, or the like.

A debulking assembly, such as a cutter 28, abrasive member, or the like, is disposed within a lumen 30 of the catheter body 22. The cutter 28 is typically rotatable within the distal portion 26 about an axis that is parallel to the longitudinal axis of the distal portion 26 of catheter 20 and axially movable along the longitudinal axis. The cutter 28 can access target tissue through a side opening window 32 which is typically large enough to allow the cutter 28 to protrude through and move out of the window 32 a predetermined distance. The cutter is coupled to a cutter driver 34 through a coiled drive shaft 36. Actuation of a movable actuator or other input device 38 can activate the drive shaft 36 and cutter, move cutter 28 longitudinally over a cam so as to deflect the distal portion and move the cutter 28 out of cutting window 32. Camming of the cutter 28 can cause the distal portion 26 to pivot or deflect relative to the proximal portion 24 so as to deflect and urge the cutter into the tissue in the body lumen.

In some embodiments, the distal portion 26 of the catheter may be moved to an angled or offset configuration from the longitudinal axis of the proximal portion 24 of the catheter and the cutter 28. In some embodiments, the cutter 28 can also be deflected off of the axis of the proximal and/or distal portion of the catheter. Moving the distal portion 26 to an angled/offset position may cause a portion of the catheter to urge against a target tissue, may expose the cutter 28 through the window 32 or both, in various embodiments.

In catheters 20 of the present invention, proximal portion 24 is typically relatively flexible and distal portion 26 is typically relatively rigid. Additionally, many embodiments include a flexible distal tip 42. The flexible proximal portion 24 of the catheter is typically a torque shaft and the distal portion 26 is typically a rigid tubing. The torque shaft 24 facilitates transportation of the catheter body 22 and cutter 28 to the diseased site. The proximal end of the torque shaft 24 is coupled to a proximal handle 40 and the distal end of the torque shaft is attached to the distal, rigid portion 26 of the catheter through the connection assembly 27. The drive shaft 36 is movably positioned within the torque shaft 24 so as to rotate and axially move within the torque shaft 24. The drive shaft 36 and torque shaft 24 are sized to allow relative movement of each shaft without interfering with the movement of the other shaft. The catheter body will have the pushability and torqueability such that torquing and pushing of the proximal end will translate motion to the distal portion 26 of the catheter body 22.

Figure 1A:
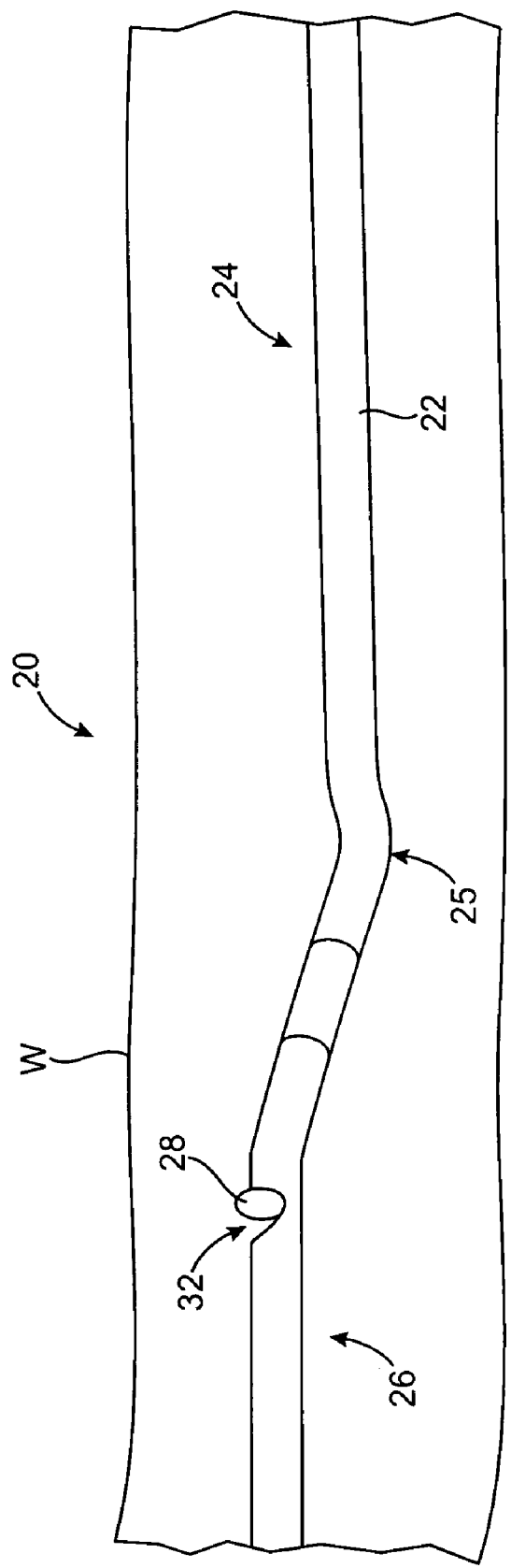
FIG. 1A is a side view of a portion of a debulking catheter as in FIG. 1, where the body has a rigid distal portion with a bend, according to one embodiment of the present invention.

Referring now to FIG. 1A, a catheter 20 as in FIG. 1 may have a flexible proximal portion 24 which additionally includes urging means 25. As shown in FIG. 1A, urging means 25 may comprise a rigid bent or curved shape towards the distal end of proximal portion 24, which may help urge the cutter 28 or other debulking apparatus toward a wall of a body lumen to enhance treatment. Such a rigid bend increases the working range of the catheter by allowing the cutter to be urged into a lumen wall across a wider diameter lumen.

In other embodiments, urging means 25 may take many other suitable forms. For example, a similar result to the rigid bend may be achieved by including a rigid distal portion that is not permanently bent but that is more rigid on one side than on the opposite side of catheter body 22. Thus, when proximal tension is applied to the proximal portion 24, as when proximal force is applied to the debulking apparatus to expose the cutter 28 through the window 32, the urging means 25 (i.e., the rigid distal portion of proximal portion 24) will cause the catheter body 22 to bend toward the less rigid side. The less rigid side will typically be the same side as the window 32, so that the window 32 and/or the cutter 28 will be urged against a wall of a body lumen by the bend. In still other embodiments, a shaped element may be introduced into catheter body to act as urging means 25. Any suitable urging means is contemplated.

Figure 2:
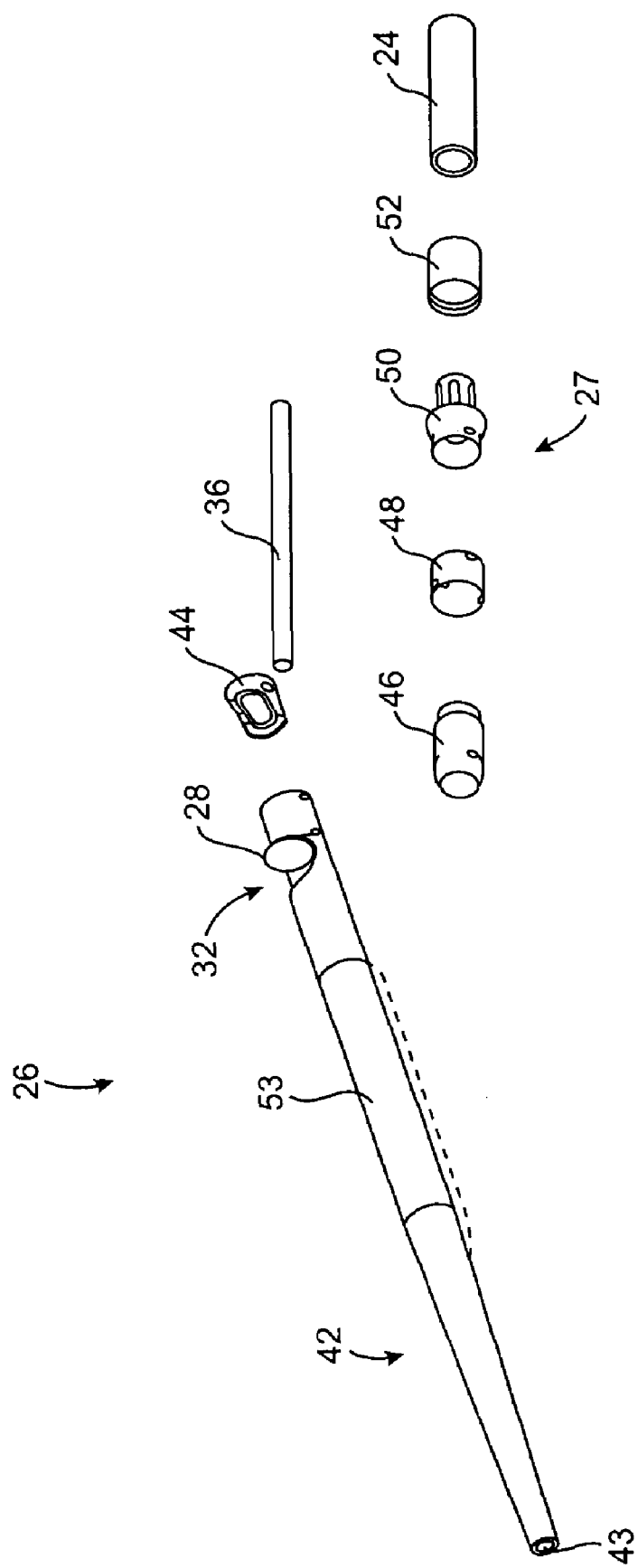
FIG. 2 is an exploded view of an exemplary distal portion of the debulking catheter of the present invention.

FIG. 2 illustrates an exploded view of a distal end of the catheter. In such embodiments, the catheter 10 includes a connection assembly 27, a rigid housing 26, a distal tip 42 that at least partially defines a collection chamber 53 for storing the severed atheromatous material, and a lumen that can receive the guidewire. The distal tip 42 can have a distal opening 43 that is sized to allow an imaging guidewire or conventional guidewire (not shown) to be advanced distally through the tip. In some embodiments, the distal tip 42 may also include a distal guidewire lumen (not shown) for allowing passage of a guidewire. For example, some embodiments may include a distal guidewire lumen having a length of between about 1.0 cm and about 5.0 cm, and preferably between about 2.0 cm and about 3.0 cm. Such a distal guidewire lumen may be used alone or in conjunction with a proximal guidewire lumen located on another, more proximal, portion of the catheter 20.

In embodiments including a distal guidewire lumen and a proximal guidewire lumen, the distal lumen may be configured to partially telescope within a portion of the proximal guidewire lumen, or vice versa. Such telescoping lumens may be used in embodiments where the distal portion 26 of catheter body 22 is movable relative to the proximal portion 24. A telescoping lumen may enhance performance of the catheter 20 by allowing a guidewire to be maintained largely within a lumen and to not be exposed within the body lumen being treated. Telescoping lumens may have any suitable diameters and configurations to allow for sliding or otherwise fitting of one lumen within another.

A ramp or cam 44 can at least partially fit within the distal portion 26. As will be described in detail below, in many embodiments proximal movement of the cutter 28 over the ramp 44, causes the deflection of the distal housing 26 and guides cutter 28 out of cutting window 32. (In other embodiments, a ramp may be used to deflect the distal portion without extending the cutter out of the window.) Attached to the ramp 44 is a housing adaptor 46 that can connect one or more articulation member 48 to the distal tip to create an axis of rotation of the distal portion 26. The housing adaptor 46 and articulation member 48 allow the distal end of the catheter to pivot and bias against the body lumen. In the illustrated embodiment there are only one housing adaptor 46 and one articulation member 48, but it should be appreciated that the catheters of the present invention can include, two, three, or more joints (e.g., axis of rotation), if desired. Moreover, the axes of rotation can be parallel or nonparallel with each other.

The catheter can also include a shaft adaptor 50 and collar 52 to couple articulation member 48 to the torque shaft 22. Shaft adaptor 50 can connect the housing to the torque shaft and collar 52 can be placed over a proximal end of the shaft adaptor and crimped for a secure attachment. It should be appreciated by one of ordinary skill in the art that that while one exemplary catheter of the present invention has the above components that other catheters of the present invention may not include more or fewer of the components described above. For example, some components can be made integral with other components and some components may be left out entirely. Thus, instead of having a separate ramp 44, the ramp may be integrated with the distal tip to direct the cutter out of the cutting window.

As shown in FIGS. 3-5, the cutters 28 of the present invention will generally be movable between two or more positions. During advancement through the body lumen, the cutter will generally be in a neutral position (FIGS. 3A and 3B) in which the cutter 28 is distal of cutting window 32. In some embodiments, an imaging device (not shown) can be coupled to cutter 28 so as to image the body lumen through cutting window 32 when cutter 28 is in the neutral position. Once the catheter 20 has reached the target site, the cutter 28 can be moved to an open position (FIGS. 4A and 4B) in which the cutter 28 is moved to a proximal end of the cutting window 32 and will extend out of the cutting window 32 a distance $L_1$ beyond an outer diameter D of the rigid portion 26. In most embodiments, in the open position, the cutter will have deflected the distal portion and the cutter's axis of rotation will generally be in line with connection assembly 27 but angled or offset from longitudinal axis of the distal portion of the catheter body.

Optionally, in some embodiments, cutter 28 can be moved to a packing position, in which the cutter is moved distally, past the neutral position, so as to pack the severed tissue into a distal collection chamber 53 (FIGS. 5A and 5B). It should be appreciated however, that while the exemplary embodiment moves the cutter to the above described positions, in other embodiments of the present invention the cutter can be positioned in other relative positions. For example, instead of having the neutral position distal of the cutting window, the neutral position may be proximal of the window, and the open position may be along the distal end of the cutting window, or the like.

Figure 4A:
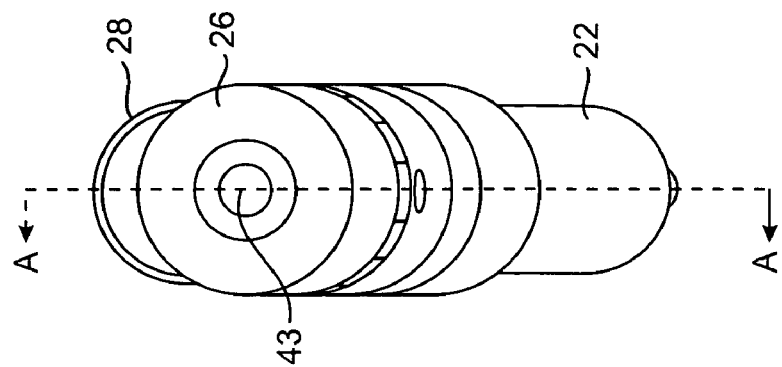
FIG. 4A is an end view of the distal portion of the debulking catheter of FIG. 1 in which the cutter is in an open position outside of the cutting window.
Figure 4B:
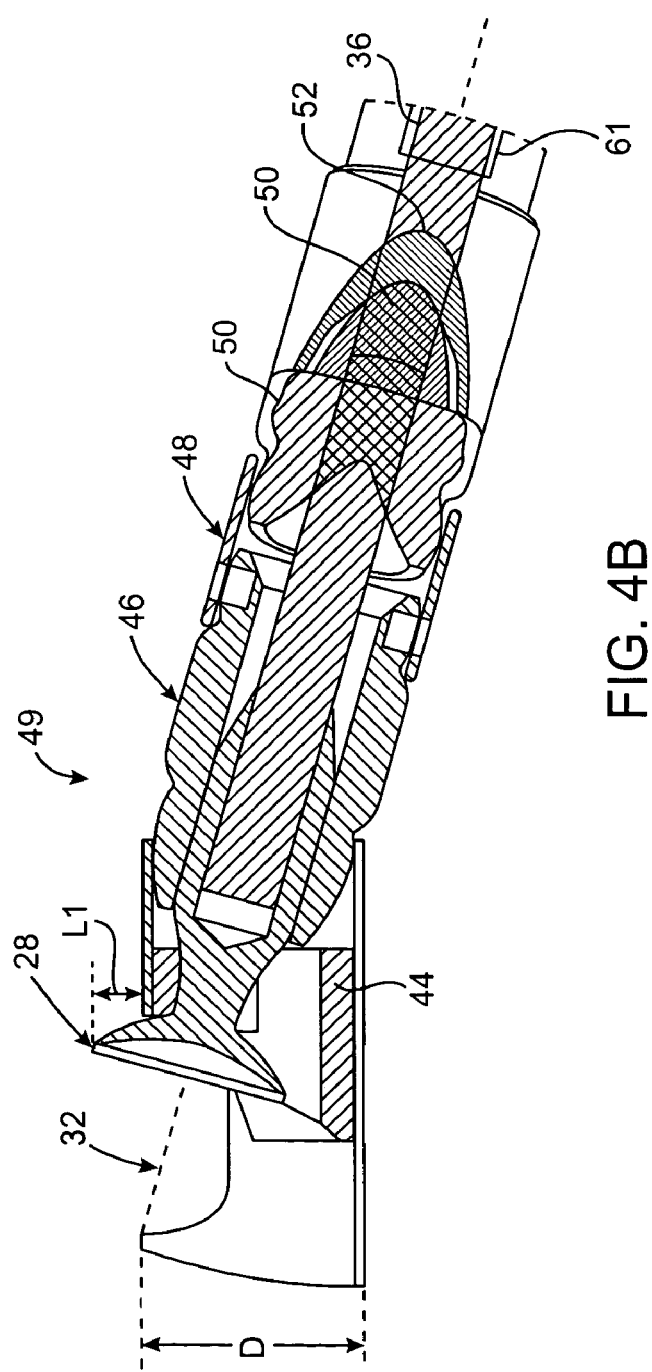
FIG. 4B is a sectional view along Line A-A of FIG. 4A.

Referring again to FIGS. 4A and 4B, the interaction of the components of the rigid distal portions 26 in one exemplary embodiment of the present invention will be further described. As shown in FIG. 4B, the cutting window 32 is typically a cutout opening in the distal portion 26. While the size of the cutting window 32 can vary, the cutting window should be long enough to collect tissue and circumferentially wide enough to allow the cutter to move out of the cutting window during cutting, but sized and shaped to not expel emboli into the vasculature. Cams or ramp 44 (shown most clearly in FIG. 4B) can be disposed in the distal portion of the catheter body to guide or otherwise pivot the cutter 28 out of the cutting window 32 as the cutter 28 is pulled proximally through tensioning of drive shaft 36.

A joint is located proximal to the cutting window 32 to provide a pivot point for camming of the distal portion 26 relative to the proximal portion 24. The bending at a flexible joint 49 is caused by the interaction of cams or ramps 44 with cutter 28 and the tensile force provided through drive shaft 36. In the exemplary configuration, the joint includes a housing adaptor 46 that is pivotally coupled to the distal rigid portion 26. As shown in FIGS. 4A and 4B, the resulting pivoting of the rigid distal portion 26 relative to the proximal portion causes a camming effect which urges the distal housing against the body lumen wall without the use of urging means (e.g., a balloon) that is positioned opposite of the cutting window. Thus, the overall cross sectional size of the catheter bodies can be reduced to allow the catheter to access lesions in smaller body lumens. In exemplary embodiments, the distal housing can deflect off of the axis of the proximal portion of the catheter typically between 0° degrees and 30° degrees, usually between 5° degrees and 20° degrees, and most preferably between 5° degrees and 10° degrees. The angle of deflection relates directly to the urge. Urge, however, does not necessarily relate to force but more to the overall profile of the catheter. For example, the greater the angle of deflection, the larger the profile and the bigger the lumen that can be treated. The ranges were chosen to allow treatment of vessels ranging from less than 2 mm to greater than 3 mm within the limits of mechanical design of the components. It should be appreciated however, that the angles of deflection will vary depending on the size of the body lumen being treated, the size of the catheter, and the like.

In some embodiments, the deflection of the distal portion 26 of the catheter urges the cutter into position such that distal advancement of the entire catheter body can move the rotating cutter through the occlusive material. Because the cutter is moved a distance $L_1$ beyond the outer diameter of the distal portion of the catheter and outside of the cutting window, the user does not have to invaginate the tissue into the cutting window. In some embodiments, for example, the cutter can be moved between about 0.025 mm and about 1.016 mm, and preferably between about 0.025 mm and about 0.64 mm, beyond the outer dimension of the distal housing. It should be appreciated that the cutter excursion directly relates to the depth of cut. The higher the cutter moves out of the cutting window the deeper the cut. The ranges are chosen around efficacy without risk of perforation of the body lumen.

Figure 3C:
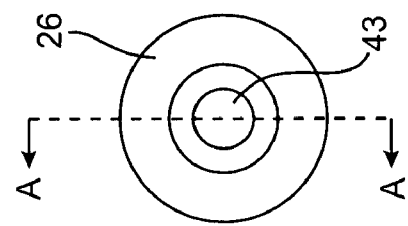
FIGS. 3C and 3D are views of the distal portion of a debulking catheter, where the distal portion has a locking shuttle mechanism.
Figure 3D:
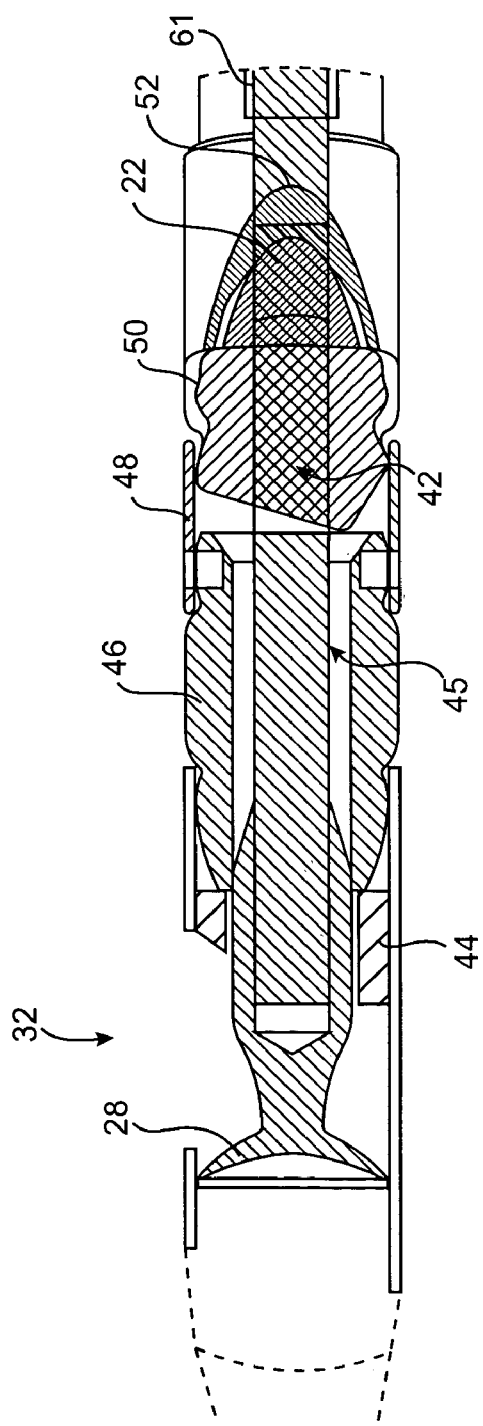
Figure 4C:
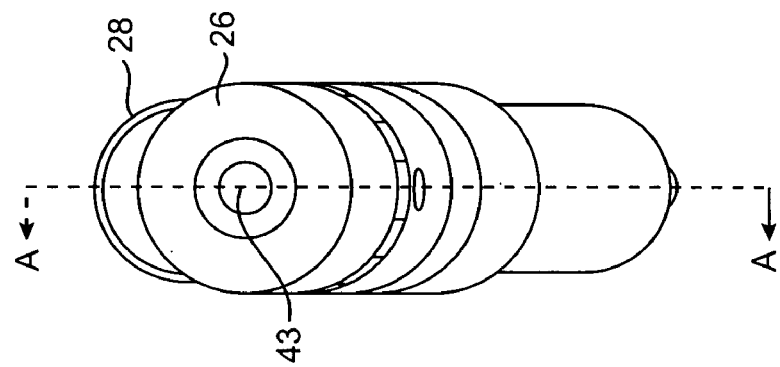
FIGS. 4C and 4D are views of the distal portion of a debulking catheter, where the distal portion has a locking shuttle mechanism.
Figure 4D:
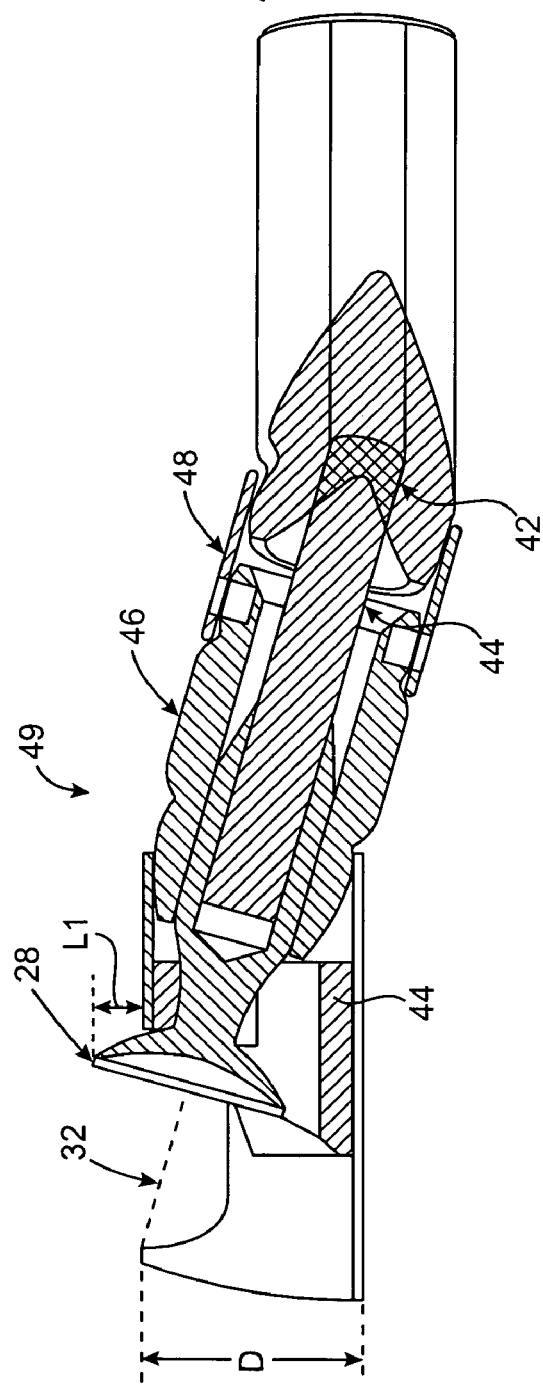

Some embodiments of the catheter include a shuttle mechanism or other similar mechanism for temporarily locking the catheter in a cutting position. FIGS. 3C and 3D illustrate such an embodiment in the neutral, non-cutting position. Such embodiments generally include a shuttle member 45 and a shuttle stop member 42. The shuttle stop member 42 is typically disposed at an angle, relative to a longitudinal axis through the catheter. FIGS. 4C and 4D show the same embodiment in the cutting position. When the cutter 28 is moved into the cutting position in such embodiments, the shuttle member 45 falls into the shuttle stop member 42 and thus locks the debulking apparatus in a cutting position. To unlock the debulking apparatus, the cutter 28 may be advanced forward, distally, to release the shuttle member 45 from the shuttle stop member 42.

Some embodiments including a shuttle mechanism will also include two joints in catheter body 22. Thus, catheter body 22 will include a proximal portion 26, a distal portion 24 and a middle portion. When shuttle mechanism is activated to expose cutter 28 through window 32, the middle portion may orient itself at an angle, relative to the proximal and distal portions, thus allowing cutter to be urged towards a side of a lumen. Such a two-jointed configuration may provide enhanced performance of the catheter 20 by providing enhanced contact of the cutter 28 with material to be debulked from a body lumen.

Pushing the entire catheter across a lesion removes all or a portion of the lesion from the body lumen. Severed tissue from the lesion is collected by directing it into a collection chamber 53 in the tip via the cutter 28. Once the catheter and cutter 28 have moved through the lesion, the cutter 28 can be advanced distally to a "part off position" in which the cutter is moved back into the cutting window 32 (FIG. 3B). The tissue is collected as the severed pieces of tissue are directed into a collection chamber 53 via the distal movement of cutter 28 and catheter. The collection chamber 53 of the tip and distal portion 26 acts as a receptacle for the severed material, to prevent the severed occlusive material from entering the body lumen and possibly causing downstream occlusions. The cutter 28 can interact with the distal edge of the cutting window to part off the tissue and thereafter pack the severed tissue into collection chamber 53 (FIG. 3B). In exemplary embodiments, the driver motor can be programmed to stop the rotation of the cutter at the part off position so that the cutter 28 can move to a third position (FIG. 5B) and pack the material in the collection chamber in the tip without rotation. Typically, the collection chamber 53 will be large enough to allow multiple cuts to be collected before the device has to be removed from the body lumen. When the collection chamber is full, or at the user's discretion, the device can be removed, emptied and reinserted over the guidewire via a monorail system, as will be described below.

In various embodiments, enhancements to the collection chamber 53 may be included. For example, in some embodiments the collection chamber 53 may be configured to be partially or completely translucent or radiolucent and a portion of the catheter surrounding or adjacent to the window 32 will be radiopaque. This combination of radiolucent collection chamber 53 and radiopaque material adjacent window 32 will enhance the ability of a user to determine how full the collection chamber 53 is, because the fullness of the collection chamber will be directly related to the distance the cutter 28 can advance forward into the collection chamber 53. By facilitating the assessment of collection chamber filling, these embodiments will reduce the need for manually withdrawing the catheter to examine the collection chamber 53.

In some embodiments, the collection chamber 53 may connect to the rigid housing by means of interlocking components, which interlock with complementary components on the rigid housing. Such components may resemble a screw-in configuration, for example. Interlocking components will provide a stable connection between the collection chamber 53 and the rigid housing while not increasing the outer diameter of either the chamber 53 or the housing. Generally, collection chamber 53 may be given any suitable configuration, shape or size. For example, collection chamber 53 in FIGS. 6-8 has a helical configuration. Alternatively, collection chamber 53 may include a series of circular members, straight linear members, one solid cylindrical or cone-shaped member or the like.

Figure 6:
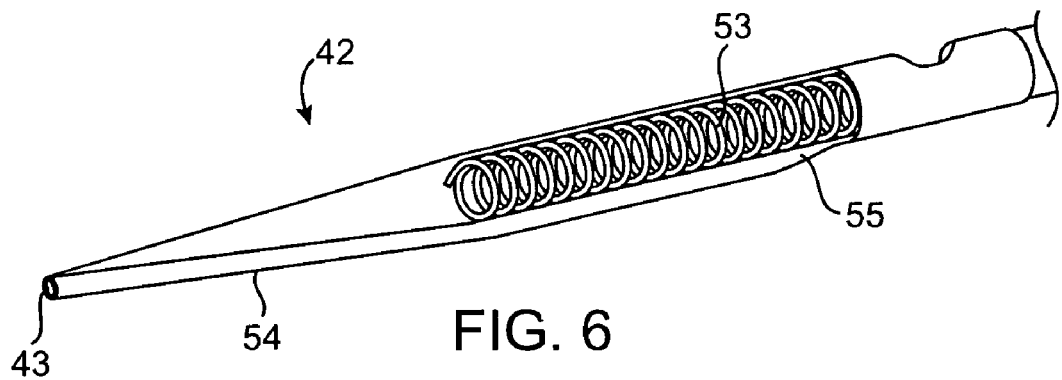
FIGS. 6 to 8 illustrate a monorail delivery system of the present invention.
Figure 7:
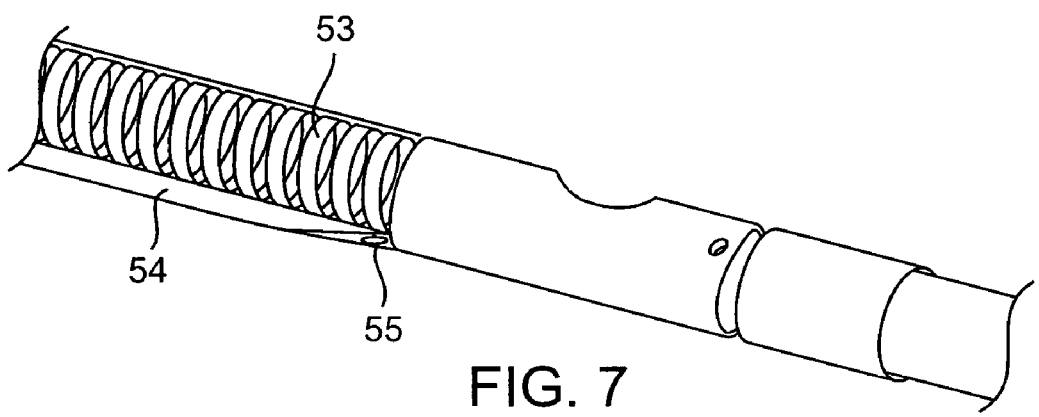
Figure 8:
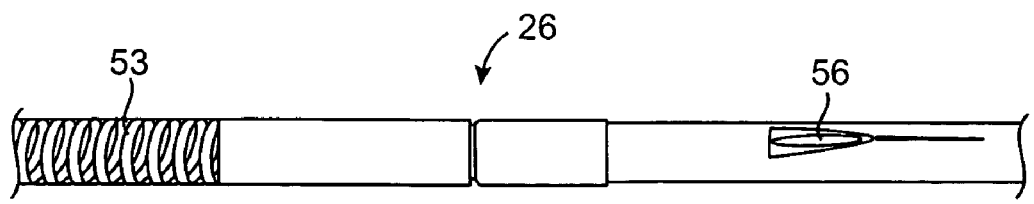

FIGS. 6 through 8 illustrate one exemplary monorail delivery system to assist in positioning the cutter 28 at the target site. For example, tip 42 of the catheter can include a lumen 54 having a distal opening 43 and a proximal opening 55 that is sized to receive a guidewire, having a diameter of about 0.014 in., about 0.018 in., about 0.032 in. or any other suitable diameter.

As shown in FIG. 8, the flexible proximal portion of the catheter body may also include a short lumen 56 (e.g., about 12 centimeters in length). In some embodiments, however, the guidewire lumen 56 may be disposed within or outside the flexible proximal portion of the catheter body and run a longer or shorter length, and in fact may run the entire length of the flexible portion 24 of the catheter body. In use, the guidewire can be disposed within lumen 56 on the flexible portion of the catheter body and exit the lumen at a point proximal to the rigid portion 26 of the catheter. The guidewire can then re-enter a proximal opening 55 in the tip lumen 54 and exit through distal opening 43 in the tip lumen. By moving the guidewire outside of the rigid portion 26 of the catheter body, the guidewire will be prevented from tangling with the cutter 28. Typically, tip lumen 54 will be disposed along a bottom surface of the tip and the lumen 56 will be disposed along a side of the proximal portion 22 of the catheter body so that the guidewire will be in a helical configuration. In various embodiments, however, the tip lumen 54 and the proximal lumen 56 can have any suitable combination of lengths. For example, in one embodiment the tip lumen 54 may have a length between about 1 cm and about 5 cm, more preferably between about 2 cm and about 3 cm, and the proximal lumen may have a length of between about 8 cm and about 20 cm, more preferably between about 10 cm and about 14 cm.

Figure 22A:
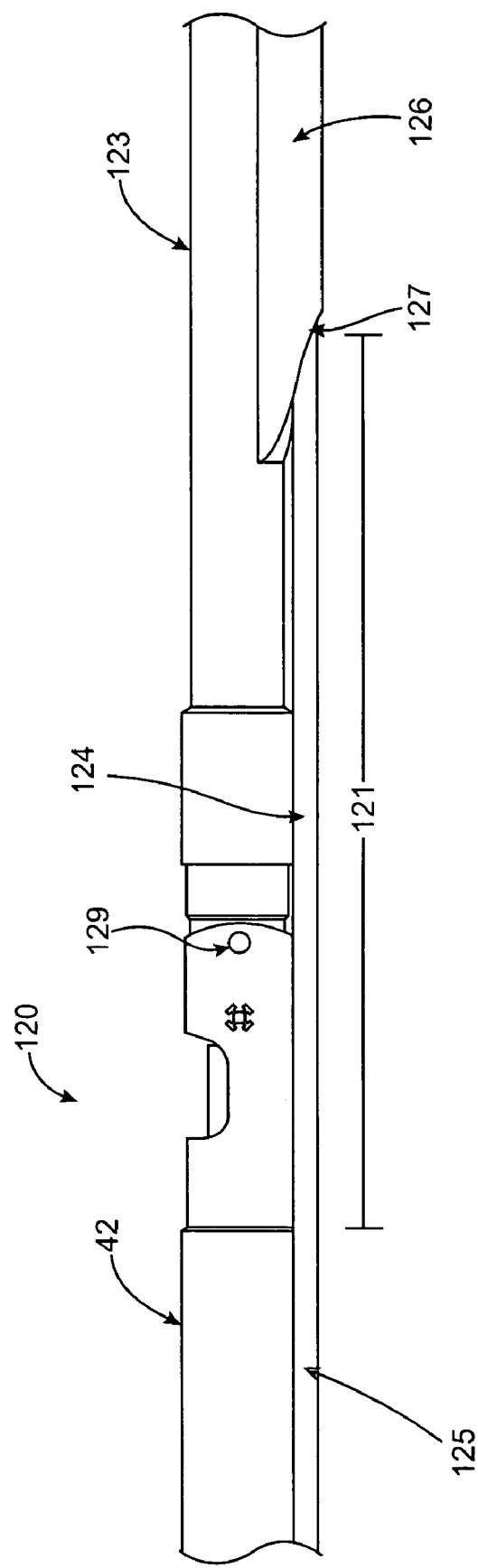
FIG. 22A shows still another device for removing material from a body lumen.
Figure 22B:
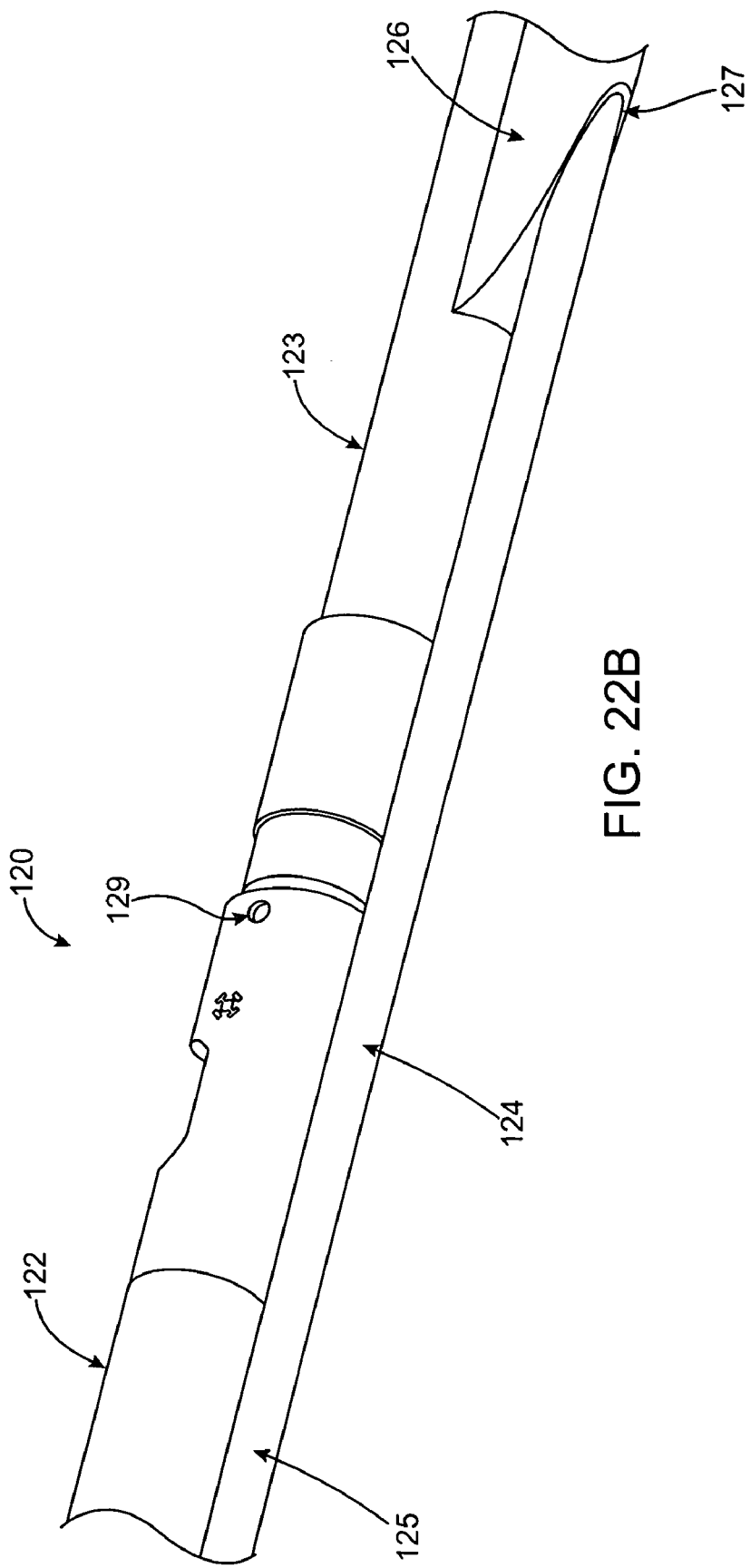
FIG. 22B shows another view of the device of FIG. 22A

Referring now to FIGS. 22A and 22B, some catheters 120 of the present invention include a proximal guidewire lumen 126 coupled with the proximal portion of the catheter body 123, and a telescoping distal guidewire lumen 124 coupled with either the distal tip 122, part of the distal portion of the catheter body, or both. The telescoping lumen 124 will typically be attached to the tip 122 or a distal portion, but will also include an unattached portion 121, which will not be directly attached to any part of the catheter body. This unattached portion 121 (or "free floating lumen") protects a guidewire from contacting a body lumen in which the device is used and also allows the device to be moved more freely, without bending or kinking the guidewire. The telescoping guidewire 124 extends within the proximal lumen 126 at the distal opening 127 of proximal lumen 126. Again, the telescoping feature allows for movement of the catheter body while preventing or reducing bending of the guidewire. For example, in some embodiments catheter 120 allows for deflection of distal tip 122 and the distal portion of the catheter 120 relative to the proximal portion 123, for example by movement about a pivot point 129. Telescoping distal lumen 124 and proximal lumen 126 allow for this movement by allowing distal lumen 124 to telescope within proximal lumen 126. At the same time, distal lumen 124 protects a guide wire from exposure to a body lumen and/or bodily fluids.

Any suitable configurations and sizes of distal lumen 124 and proximal lumen 126 are contemplated. For example, in one embodiment distal lumen 124 may telescope within proximal lumen 126 by a distance of approximately 1 cm. Furthermore, a telescoping lumen 124 may be longer than distal lumens in other embodiments. For example, telescoping lumen 124 may have a length of between about 2 cm and about 10 cm, and preferably between about 5 cm and about 8 cm. As is apparent from the drawing figures, the outer diameter of telescoping distal lumen 124 is configured to fit within the inner diameter of proximal lumen 126. Generally, any combination of sizes, lengths, diameters and shapes of distal lumen 124 and proximal lumen 126 may be used, to allow telescoping of one into another.

The catheters of the present invention can include radiopaque markers so as to allow the user to track the position of the catheter under fluoroscopy. For example, as already described, a point or area around or adjacent to the window may be made radiopaque. In other embodiments, the rigid distal portion 26 can be radiopaque and radiopaque markers can be disposed on the flexible shaft. Typically, the markers 59 will be disposed along the top, proximal to the cutting window, and on the bottom of the catheter to let the user know the position of the cutter and cutting window relative to the target site. If desired, the top and bottom markers can be different shaped so as to inform the user of the relative orientation of the catheter in the body lumen. Because the guidewire will form a helix in its transition from lumen 56 to tip lumen 54, the user will be able to view the top and bottom radiopaque markers 59 without interference from the guidewire. Some embodiments of the catheter can also include a radiopaque cutter stop 61 (FIG. 3B) that is crimped to driveshaft 36 proximal of the cutter that moves with the cutter so as to let the user know when the cutter is in the open position.

FIGS. 9A through 11D show some exemplary embodiments of the cutter 28 of the present invention. The distal portion 60 of the rotatable cutter 28 can include a serrated knife edge 62 or a smooth knife edge 64 and a curved or scooped distal surface 66. The distal portion 60 may have any suitable diameter or height. In some embodiments, for example, the diameter across the distal portion 60 may be between about 0.1 cm and about 0.2 cm. A proximal portion 68 of the cutter 28 can include a channel 70 that can be coupled to the drive shaft 36 that rotates the cutter. As shown in FIGS. 10A-10C, some embodiments of the cutters can include a bulge or bump 69 that is provided to interact with a stent so as to reduce the interaction of the cutting edge with the stent. In any of the foregoing embodiments, it may be advantageous to construct a serrated knife edge 62, a smooth knife edge 64, or a scooped distal surface 66 out of tungsten carbide.

Figure 11D:
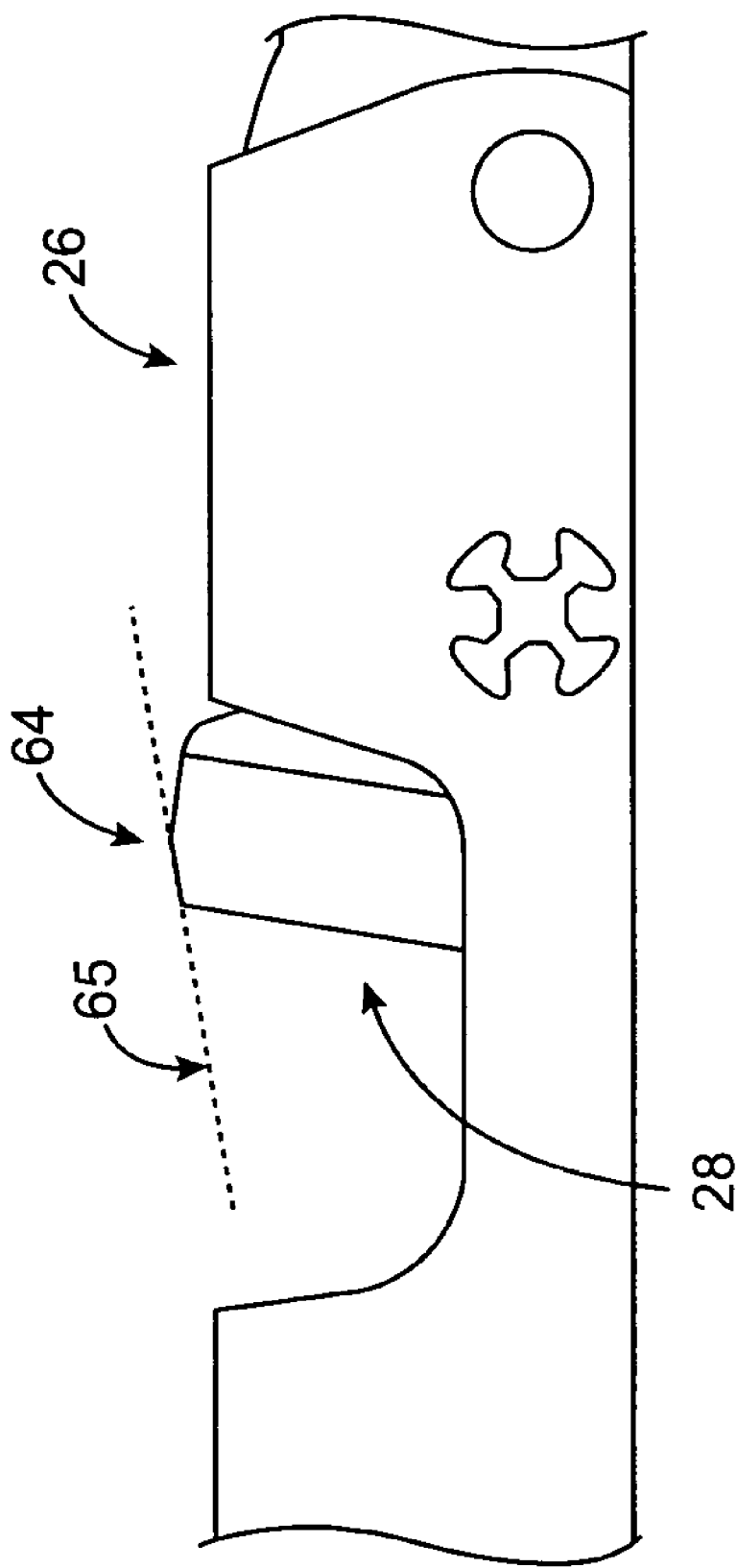
FIG. 11D is a side view of another embodiment of a cutter, shown partially within a catheter body.

Another embodiment of a cutter 28 suitable for use in the present invention is shown in side view within a catheter body distal portion 26 in FIG. 11D. In this embodiment, the cutter 28 has a beveled edge 64, made of tungsten carbide, stainless steel, titanium or any other suitable material. The beveled edge 64 is angled inward, toward the axis of rotation (or center) of the cutter 28, creating a "negative angle of attack" 65 for the cutter 28. Such a negative angle of attack may be advantageous in many settings, when one or more layers of material are desired to be debulked from a body lumen without damaging underlying layers of tissue. Occlusive material to be removed from a vessel typically has low compliance and the media of the vessel (ideally to be preserved) has higher compliance. A cutter 28 having a negative angle of attack may be employed to efficiently cut through material of low compliance, while not cutting through media of high compliance, by allowing the high-compliance to stretch over the beveled surface of cutter 28.

Figure 12:
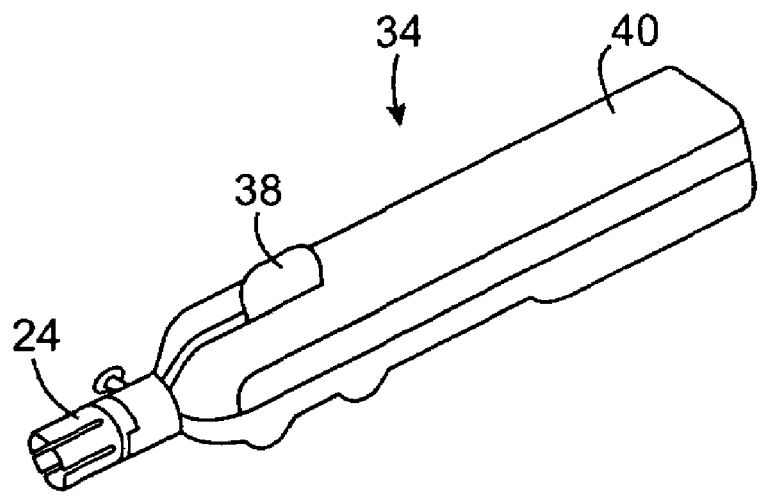
FIG. 12 illustrates a proximal handle and cutter driver of the present invention.
Figure 13:
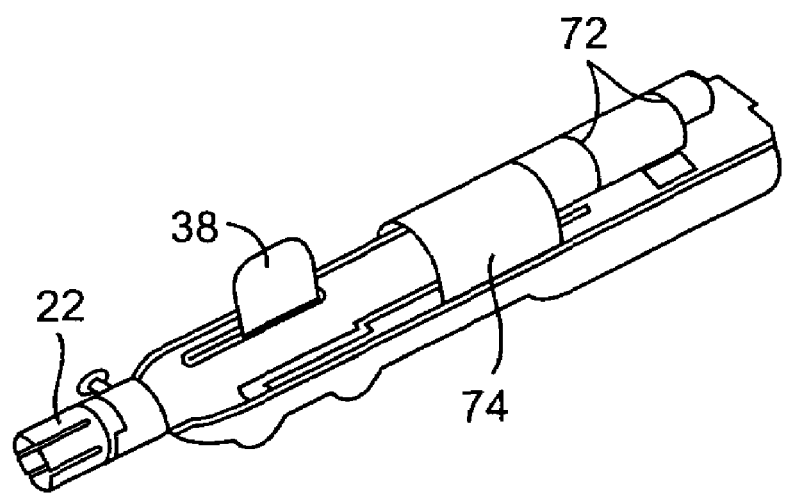
FIG. 13 illustrates a cutter driver with a handle cover removed.
Figure 14:
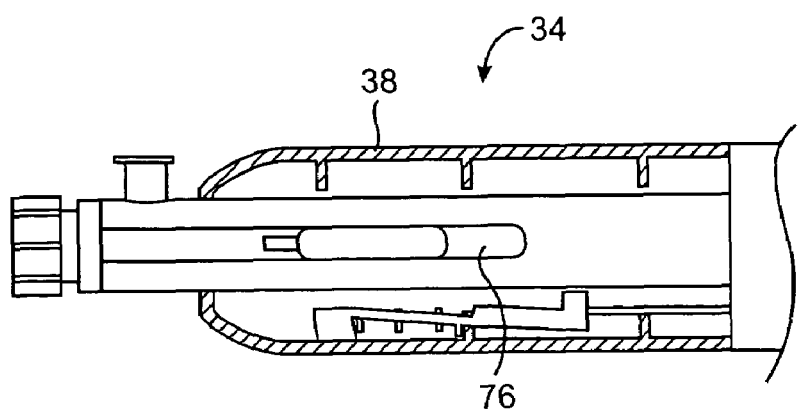
FIGS. 14 to 16 illustrate three positions of the lever for controlling the cutter.

FIGS. 12 through 16 illustrate an exemplary cutter driver 34 of the present invention. As shown in FIGS. 12 and 13, cutter driver 34 can act as the handle for the user to manipulate the catheters 20 of the present invention as well as a power source. Typically, the cutter drivers 34 of the present invention include a single input device, such as a lever 38 that controls the major operations of the catheter (e.g., axial movement to cause urging, rotation to cause cutting, and axial movement for packing). As shown in FIGS. 13 and 14, cutter driver 34 includes a power source 72 (e.g., batteries), a motor 74, a microswitch 76 for activating motor 74, and a connection assembly (not shown) for connecting the drive shaft 36 to the driver motor 74. In some embodiments, the drive motor can rotate drive shaft 36 between 1,000 rpm and 10,000 rpm or more, if desired.

Figure 15:
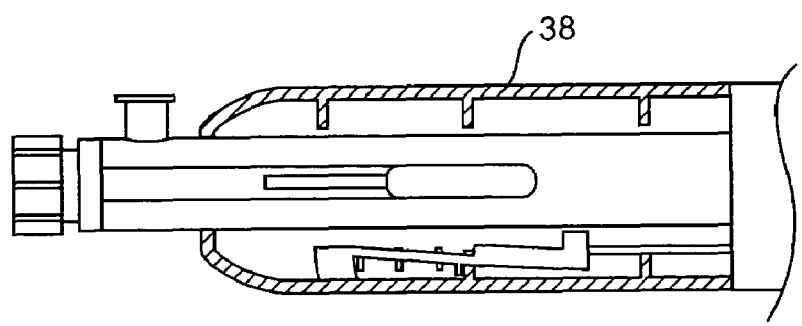
Figure 16:
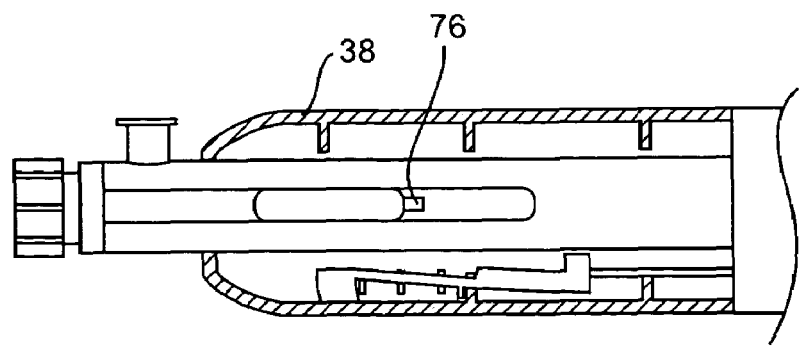

FIGS. 14 through 16 illustrate one exemplary method of operating cutter driver 34. In use, the catheter will be delivered to the target site with cutter driver unattached and the cutter in the neutral position (FIG. 3B). The cutter driver can be attached with the urge lever 38 in a neutral position (FIG. 14), which indicates that the cutter is closed, but not in a packing position. The user can then move the catheter (and cutter driver unit, if desired) to position the distal portion 26 of the catheter adjacent the target tissue. As shown in FIG. 15, to activate the rotation of the cutter, the urge lever 38 can be moved proximally from the neutral position to move the cutter proximally and out of cutting window 32 (FIG. 4B) and simultaneously depressing microswitch 76 to activate motor 74. At the end of the cutting procedure, as shown in FIG. 16, the user can push urge lever 38 completely forward to a distal position to push the cutter into a packing position (FIG. 5B). After the urge lever passes the middle of the travel, the microswitch 76 can be released so as to deactivate the cutter before reaching the packing position such that packing can occur without the cutter rotating. It should be appreciated, while the figures illustrate the use of an urge lever or thumb switch as an input device, the present invention can use other type of input devices, such as labeled buttons (e.g., close window, debulk tissue, and pack), or the like.

Advantageously, cutter driver 34 provides an automatic on/off control of the cutter 28 that is keyed to the position of the cutter. Such a configuration frees the user from the complicated task of remembering the sequence of operations to activate and deactivate the rotation and axial movement of the cutter.

While the cutter driver 34 is illustrated as a disposable battery powered unit, it should be appreciated that in other embodiments, the cutter driver can use other power sources to control the cutter driver. It should further be appreciated that other cutter drivers can be used with the present invention. While not preferred, it is possible to have separate controls to control the axial movement of the cutter and the rotation of the cutter.

Figure 17:
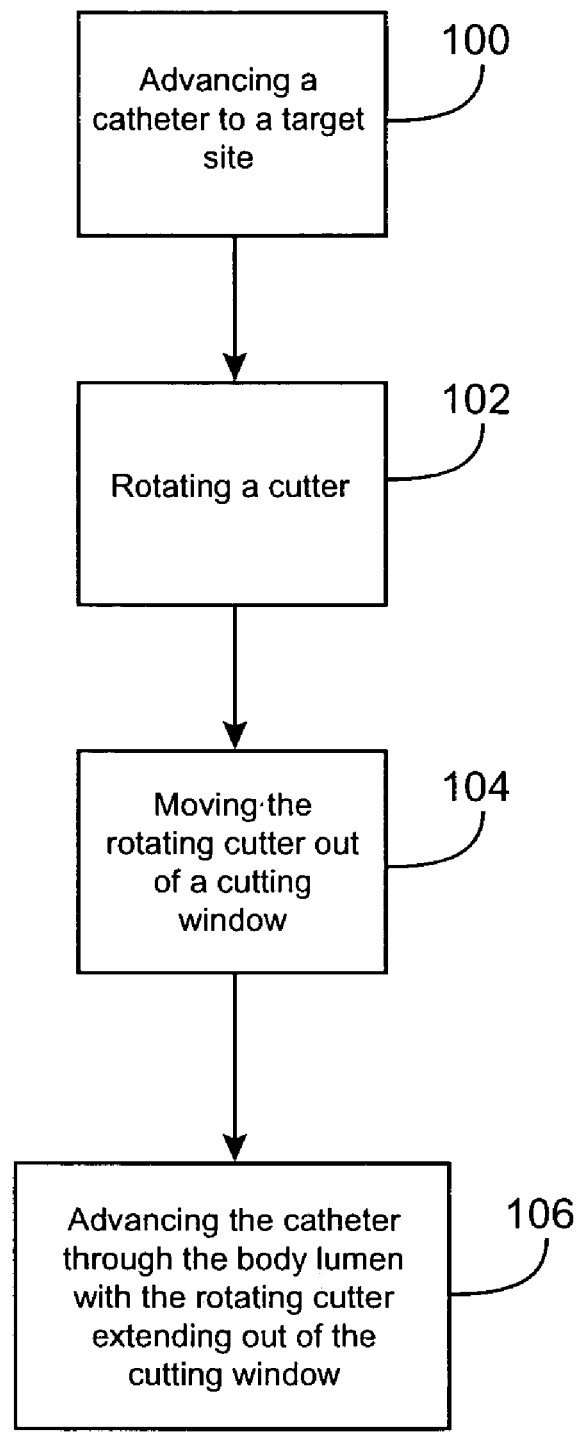
FIG. 17 is a simplified flow chart illustrating a method of the present invention.

Some exemplary methods of the present invention will now be described. One method of the present invention comprises delivering a catheter to a target site in the body lumen. A distal portion of the catheter can be deflected relative to a proximal portion of the catheter to expose a tissue debulking device in the catheter. The body lumen can be debulked with the exposed debulking device. Specifically, as shown schematically in FIG. 17, one specific method comprises advancing a catheter to a target site (Step 100). A cutter can be rotated and moved out of the cutting window (Steps 102, 104). Preferably, a distal portion of the catheter can be pivoted or deflected so as to position the cutter adjacent the target material. Thereafter, the catheter and the rotating cutter can be moved through the body lumen to remove the target material from the body lumen (Step 106).

Figure 18:
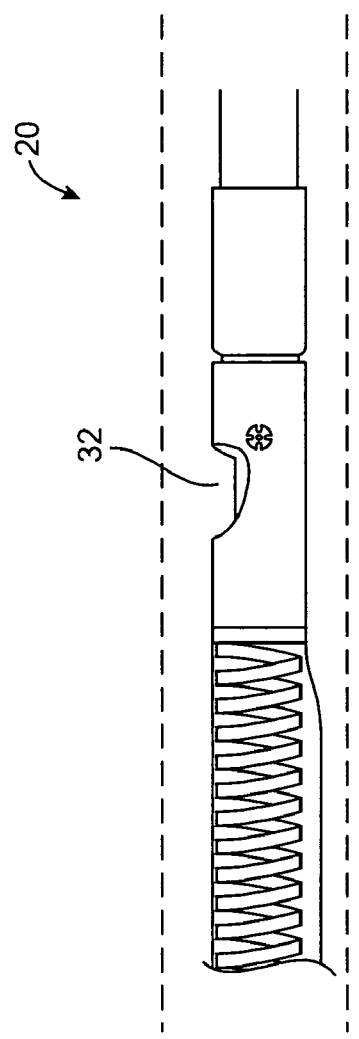
FIGS. 18 and 19 illustrate a method of the present invention.
Figure 19:
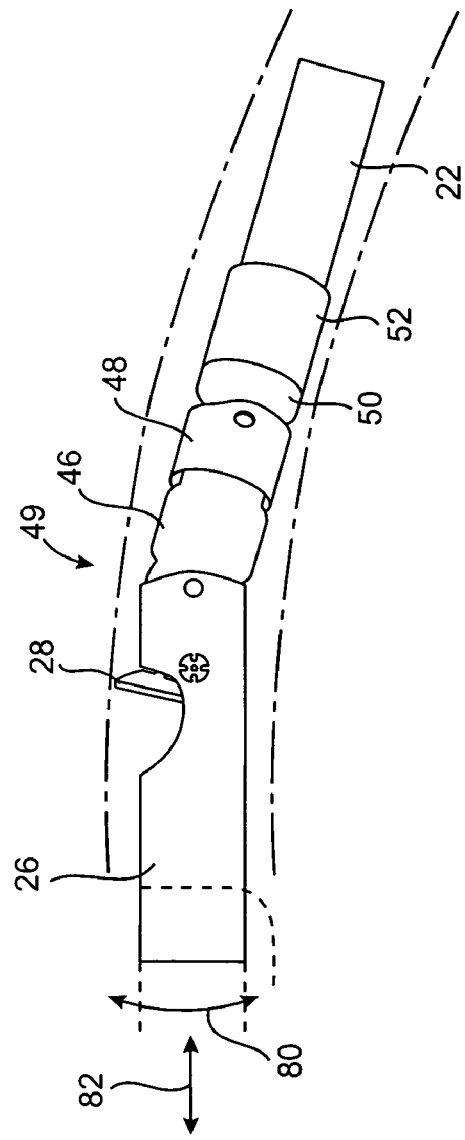

As shown in FIGS. 18 and 19, the catheter can be percutaneously advanced through a guide catheter or sheath and over a conventional or imaging guidewire using conventional interventional techniques. The debulking catheter 20 can be advanced over the guidewire and out of the guide catheter to the diseased area. As shown in FIG. 18, the window 32 will typically be closed (with the cutter or other debulking device 28 in a first, distal position). As shown in FIG. 19, catheter 20 will typically have at least one hinge or pivot connection to allow pivoting about one or more axes of rotation to enhance the delivery of the catheter into the tortuous anatomy without dislodging the guide catheter or other sheath. The cutter can be positioned proximal of the lesion. Optionally, a transducer, IVUS, or other imaging assembly can be used to verify the position of the debulking catheter.

Once the position of the catheter is confirmed, the cutter 28 will be retracted proximally and moved out of cutting window 32 to its second, exposed position. In some embodiments, movement of the cutter can deflect the distal portion of the catheter to increase the profile of the catheter at the target site. Movement of the cutter is typically caused by proximal movement of lever 38 and tensioning of drive shaft 36. Movement of the lever can be scaled to any desired ratio or a direct 1:1 ratio of movement between the handle and cutter. When the cutter is moved proximally it contacts ramp or cam surfaces so as to guide the cutter up and at least partially out of the cutting window 32. Additionally, as shown by arrow 80, the distal portion of catheter body 26 rotates about the joint 49 to provide an urging force for the cutter (and catheter body) to move toward the diseased area.

Thereafter, as shown by arrow 82 the operator can move the entire catheter body 22 through the lesion to dissect the tissue. As the cutter 28 and catheter body 22 are advanced distally through the lesion, tissue that is trapped between the cutting edge 52 and the cutting window 32 is severed from the body lumen. To part off the tissue, the operator can stop pushing the device distally and the cutter can be advanced distally inside the cutting window by advancing the handle 38. During the distal movement of the cutter, the cutter 28 rides back over the ramps 44 and directs the cutter back inside of the cutting window 32. Such movement causes the distal portion 26 of the catheter to move in line with the cutter and proximal portion 24 (FIG. 5B). When the cutter has moved to its distal position, the cutter parts off the severed tissue and urges the severed tissue inside of a collection chamber 53 in the distal tip 42. Optionally, after the cutter 28 has parted off the tissue, the lever 38 and thus the non-rotating cutter 38 can be advanced distally to pack the tissue into the collection chamber 53 (FIG. 5B). Use of the cutter to pack the severed tissue will allow the operator multiple specimens to be collected prior to removing the catheter 20 from the body lumen. When it is determined that the collection chamber is full, the catheter can be removed from the body lumen and the collection chamber can be emptied.

Figure 20:
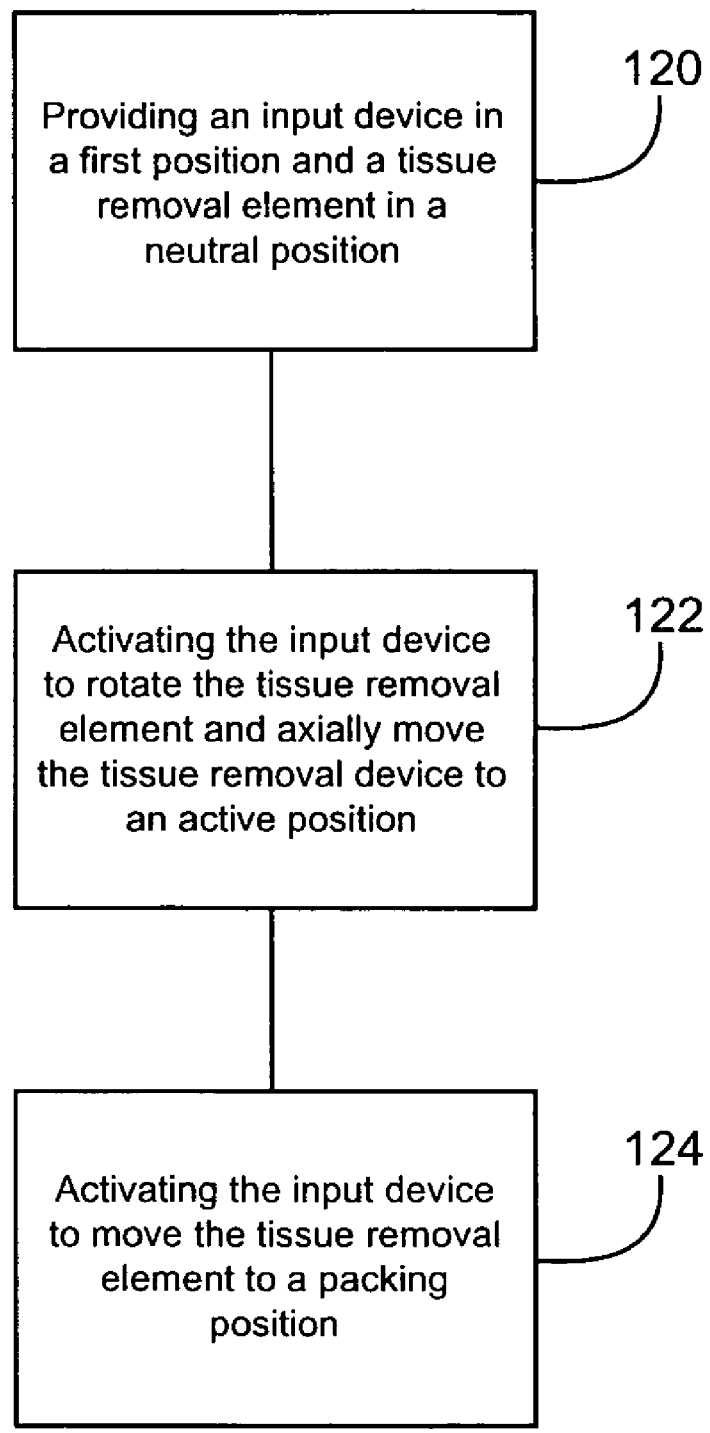
FIG. 20 schematically illustrates another method of the present invention.

In another method of the present invention, as shown in FIG. 20, an input device is disposed in a first position to position a tissue removal element in a neutral position (Step 120). The input device is activated to rotate the tissue removal element and to axially move the tissue removal device to an active position (Step 122). The input device can then be activated again to move the tissue removal element to a packing position (Step 124). In an exemplary embodiment, the input device is a lever or thumb switch that can be moved to correspond to the movement of a cutting element on the catheter. Thus, as the lever is moved proximally, the cutter is rotated and moved proximally to an open position. When the lever is moved to a distal position, the rotation of the cutter can be stopped and the cutter can be moved distally to pack severed tissue into a collection chamber.

Figure 21:
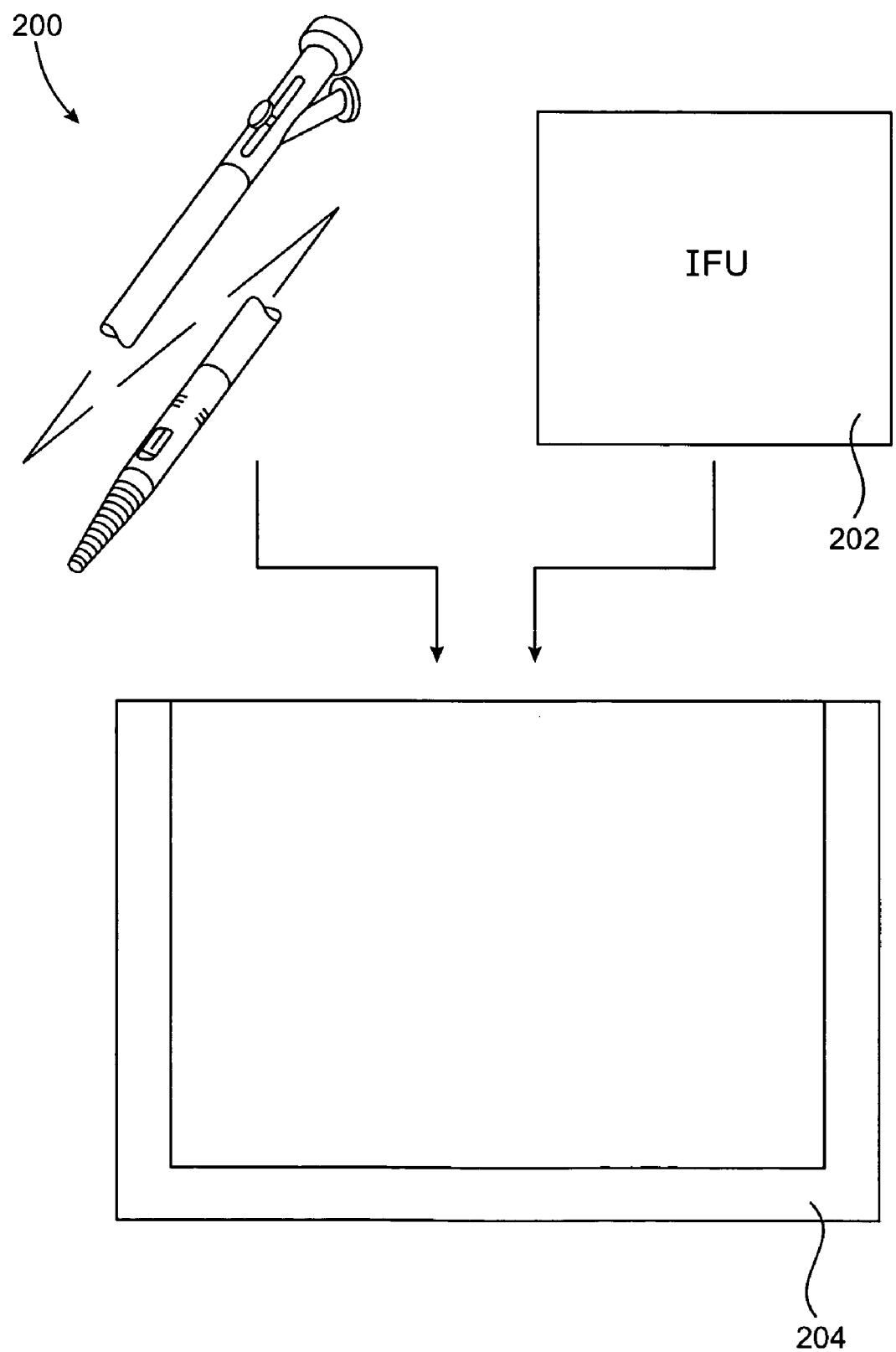
FIG. 21 illustrates a kit of the present invention.

Referring now to FIG. 21, the present invention will further comprise kits including catheters 200, instructions for use 202, and packages 204. Catheters 200 will generally be as described above, and the instruction for use (IFU) 202 will set forth any of the methods described above. Package 204 may be any conventional medical device packaging, including pouches, trays, boxes, tubes, or the like. The instructions for use 202 will usually be printed on a separate piece of paper, but may also be printed in whole or in part on a portion of the packaging 204.

Figure 23:
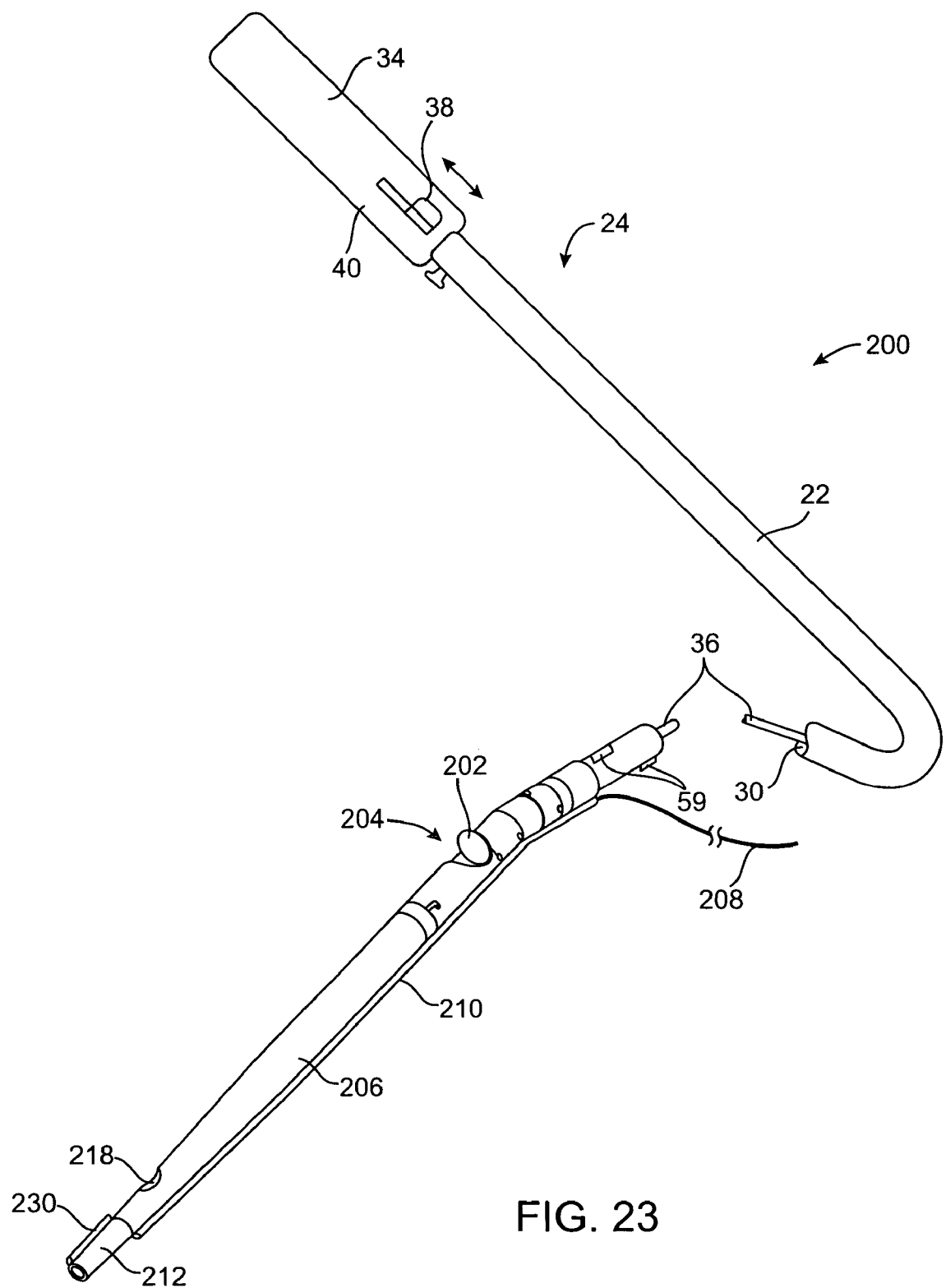
FIG. 23 shows still another device for removing material from a body lumen.
Figure 24:
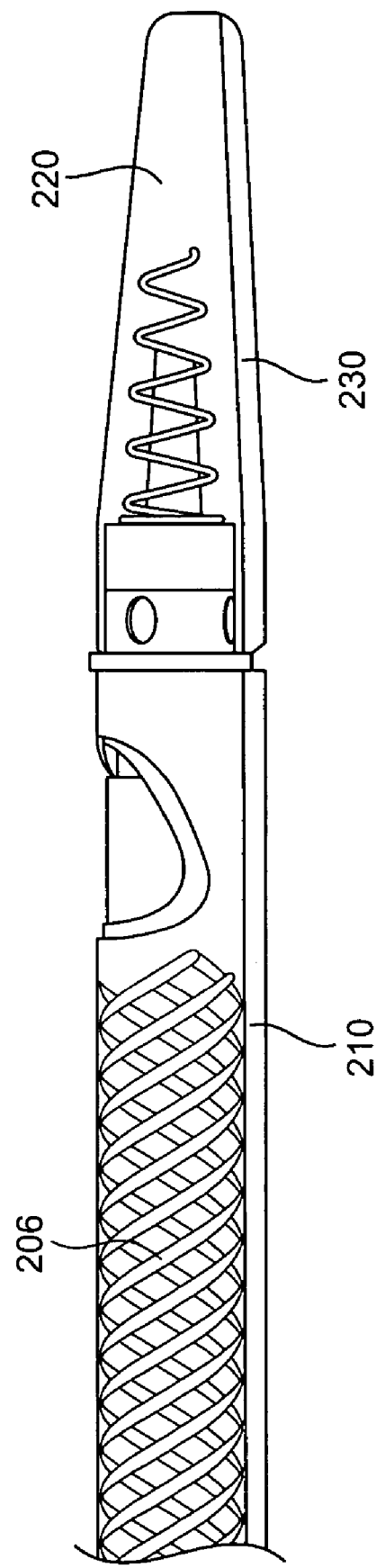
FIG. 24 shows an end of the device of FIG. 23.
Figure 26:
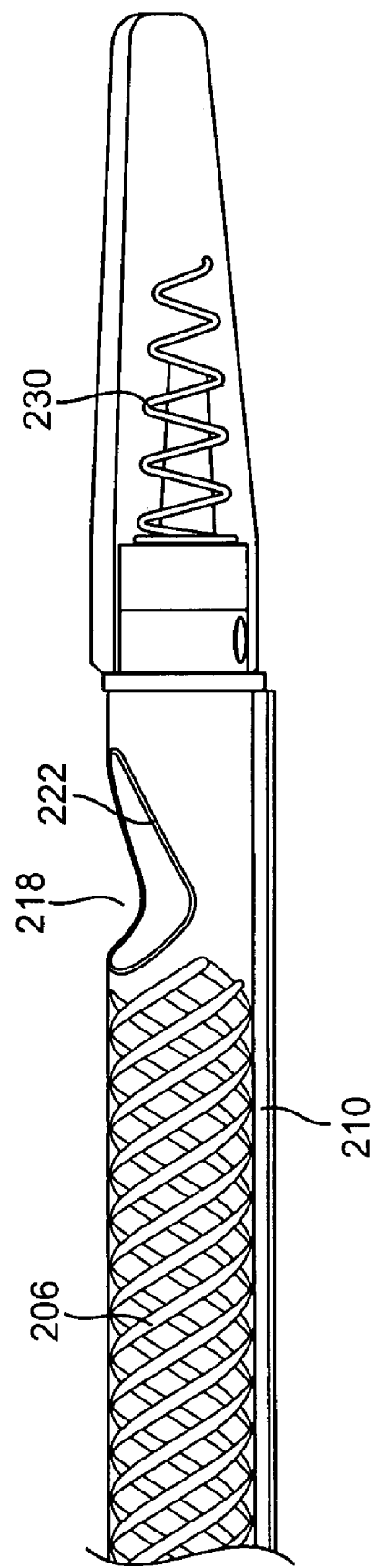
FIG. 26 shows the device of FIG. 23 with a second opening exposed by rotating the tip of the device.

Referring to FIG. 23, another atherectomy device 200 is shown. Although the atheterectomy device 200 may take on many different configurations, the atherectomy device 200 does have particular advantages over other devices as described herein and in applications and patents incorporated by reference. The catheter 200 may be constructed in any suitable manner including those methods described herein and in the patents and applications incorporated by reference.

The atherectomy device 200 has a rotating cutting element 202 which can move between the stored and working positions with a portion of the cutting element 202 becoming exposed through a first opening 204 when moving to the working position of FIG. 23. The device 200 is advanced through the blood vessel with the cutting element 202 in the working position so that material severed by the cutting element is directed through the first opening 204 and into a containment chamber 206. The device 200 is advanced over a guidewire 208 which extends through a guidewire lumen 210 on the device 200.

A distal portion 212 or tip of the device 200 may articulate or bend when the cutting element 202 moves from the stored position to the working position as described above and in the patents and applications incorporated by reference. Articulation or bending of the distal portion 212 tends to move the first opening 204 toward the wall of the blood vessel. The tip 212 may articulate in any suitable manner and various aspects of the present invention may be practiced with other features for moving the first opening 204 toward the wall of the blood vessel and orienting the cutting element 202 in an advantageous position without departing from the present invention.

The material cut by the cutting element 202 is directed through the first opening 204 and into a containment chamber 216 located distal to the first opening 204. The device 200 may be passed through the vessel a number of times with the material from each pass being stored in the containment chamber 216. When the containment chamber 216 is full, the device 200 is removed from the patient and the collection chamber 216 may be cleaned for subsequent use as described below.

Referring now to FIGS. 23-27, a second opening 218 may be created in the device 200 to help remove the material stored in the containment chamber 216. The device 200 may have a movable section 220 which is moved to expose or otherwise create the second opening 218. The movable portion 220 pivots or rotates to move between the closed position of FIG. 24 and open position of FIG. 26. For clarity, FIGS. 25 and 27 show the movable section 220 separated from the rest of the device 200 when oriented in the open and closed positions.

The movable section 220 may be located at the distal end of the containment chamber 216 near the distal tip of the device 200 opposite the first opening 204 although other locations may be used. The movable section 220 may have a curved section 222 which forms a ramp 224 to direct material out of the second opening 218 when in open position of FIG. 26. The bottom portion of the ramp 224 covers the second opening 218 when rotated into the closed position of FIG. 24. Of course, the second opening 218 may be created in any other manner without departing from various aspects of the present invention.

The guidewire lumen 210 extends along the device with a section 230 of the guidewire lumen 208 mounted to the movable section 220. In this manner, the movable section 220 may be locked by the guidewire 208. The guidewire 208 may lock the movable section 220 in another suitable way to prevent creation of the second opening 218 such as a biased locking element held in place by the guidewire 208 when resident in the guidewire lumen 210. When the device 200 is removed from the patient, the guidewire 208 is removed from the guidewire lumen 210 which permits rotation of the movable section to open the second opening 218.

Removal of the material from the containment chamber 216 is now described. The device 200 is removed from the patient and the guidewire 208 is removed from at least the section 230 of the guidewire lumen 210 along the movable section 220. The movable section 220 is then rotated to create the second opening 218.

Figure 28:
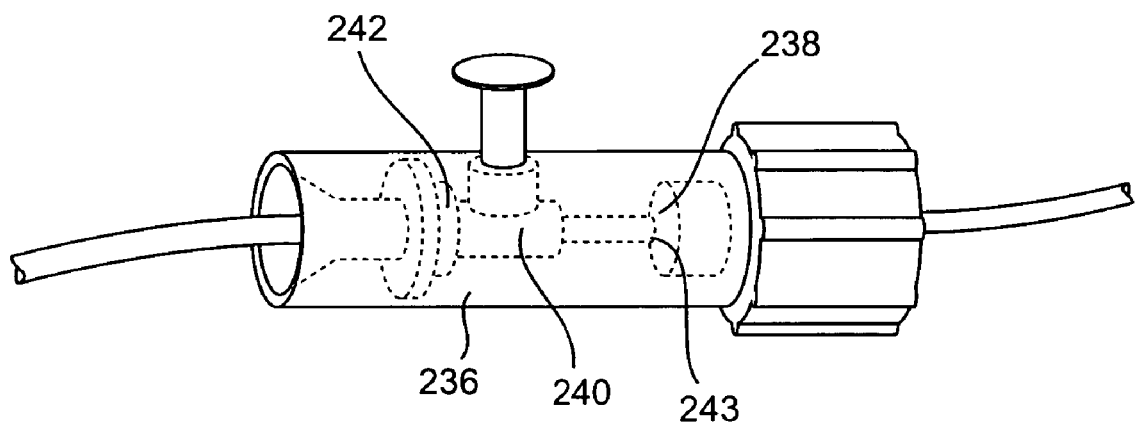
FIG. 28 shows a material removal device.
Figure 29:
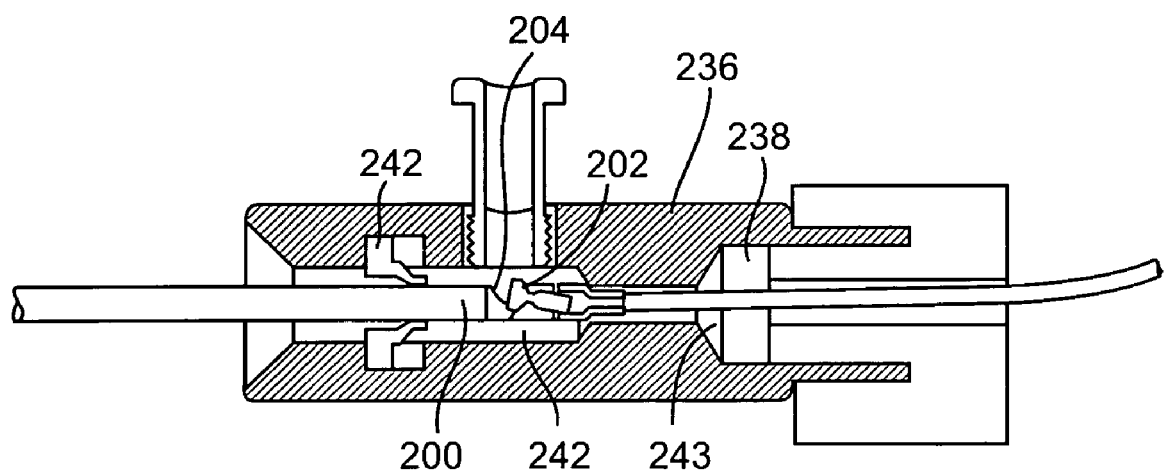
FIG. 29 is a cross-sectional view of the device of FIG. 28.
Figure 30:
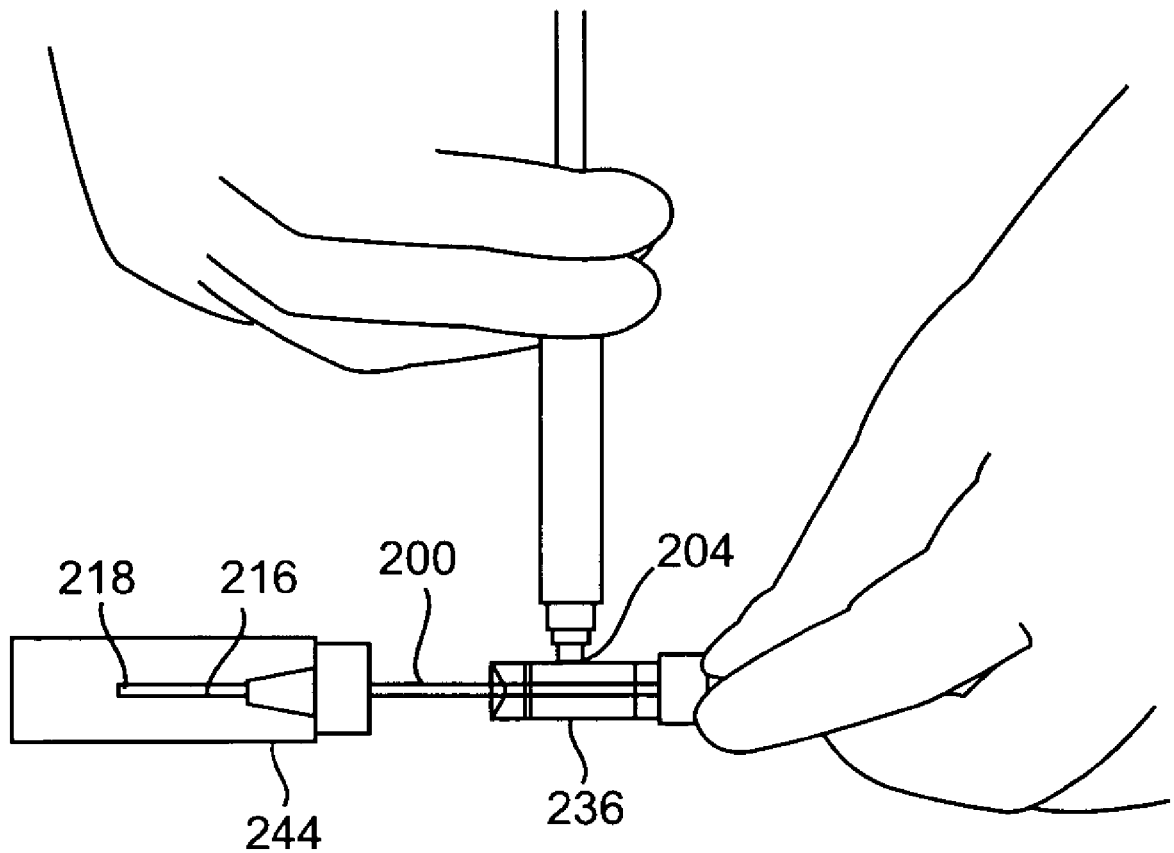
FIG. 30 shows a syringe used to inject saline through the containment chamber to remove material therefrom.

Referring to FIGS. 28-30, the containment chamber 216 may then be mounted to a material removal device 236. The material removal device 236 has a throughhole 238 which forms a cavity 240 that receives the containment chamber 216. The device 200 has a first seal 242 and a second seal which both form a circumferential seal around the shaft on both sides of the first opening 204 to isolate the first opening 204 from the second opening 218 except through the containment chamber 216. A fluid, either liquid or gas and preferably saline, is then delivered through the first opening 204 to force the material out of the second opening 218. The fluid may be delivered in any suitable manner such as with a syringe 220 or pump. The material removal device 236 may also form a seal around the second opening 218. For example, the containment chamber 216 may be introduced into a storage container 244 which has a seal 246 which isolates the second opening 218 as well. Although the first and second seals 242, 246 are shown as being independent they may also be formed by the same structure.

Figure 35:
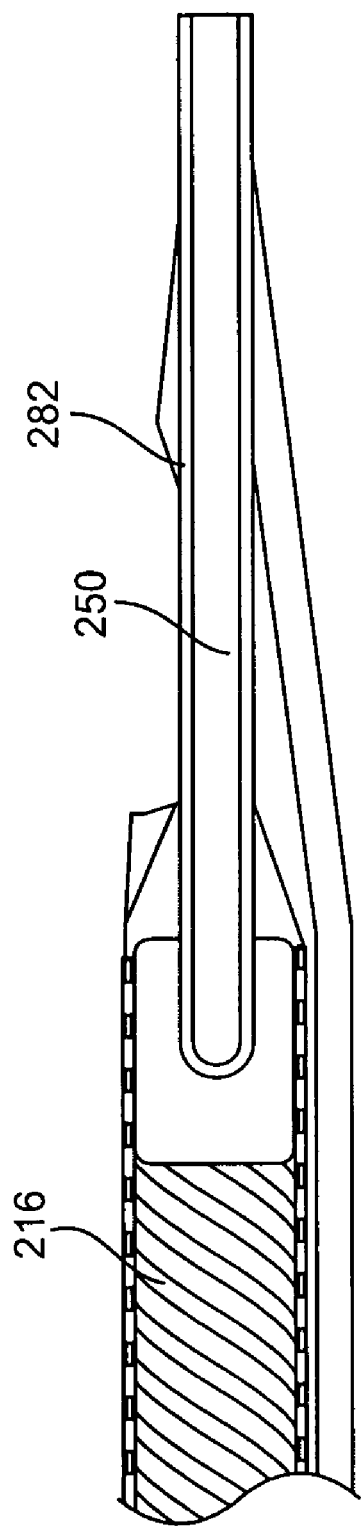
FIG. 35 shows a pusher element used to push material out of the containment chamber.
Figure 36:
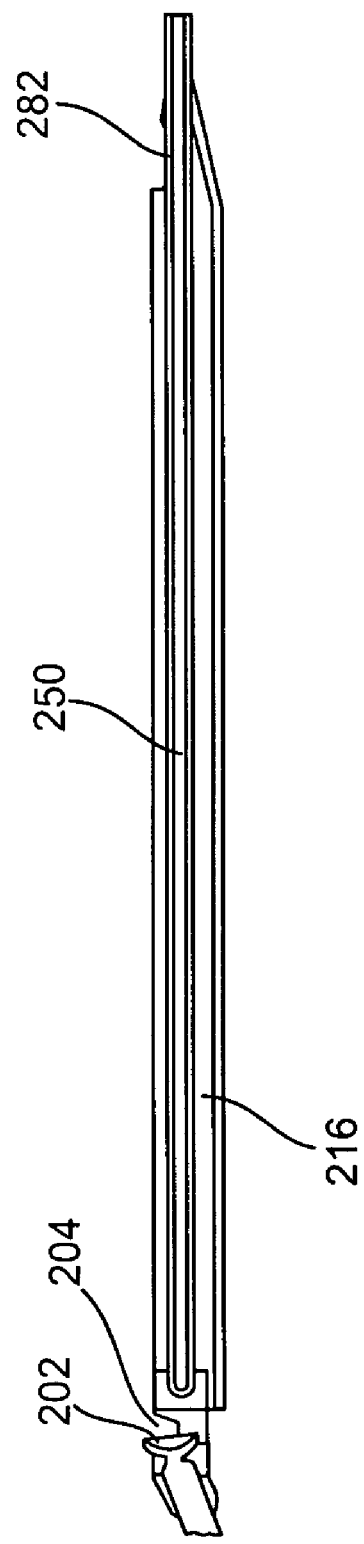
FIG. 36 shows the pusher element advanced in the containment chamber to force material out of the first opening.

Once the second opening 218 has been created, material in the containment chamber 216 may be removed in a number of different ways. Referring to FIGS. 35 and 36, for example, a separate pusher 250 may be advanced into the containment chamber 216 to force material out of one of the openings 204, 218. The various methods may be combined, of course, to clear material from the containment chamber 216. For example, the cutting element 202 or a pusher element 250 (see FIGS. 35 and 36) may be used before, during or after use of the fluid to move the material from the containment chamber 216.

Figure 31:
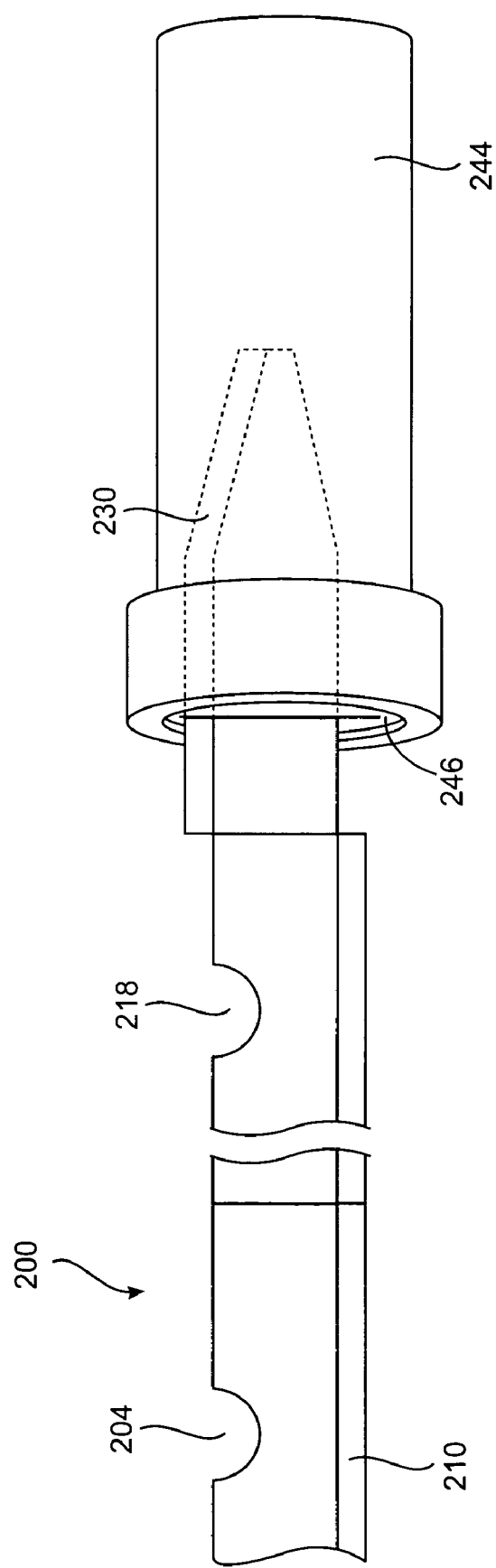
FIG. 31 shows a storage container which is used to store the material removed from the patient.
Figure 32:
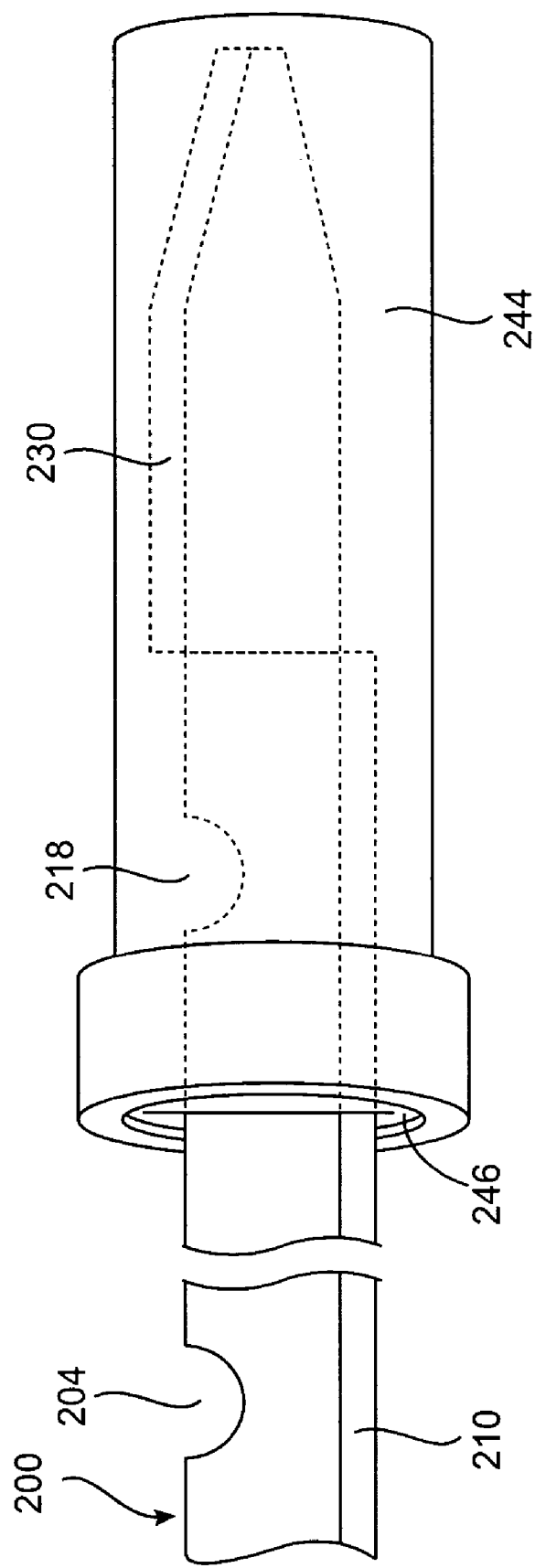
FIG. 32 shows the containment chamber inserted into the storage container.

The material may simply be discarded in the appropriate manner after removal from the device. Alternatively, the material may also be saved in the storage container 244. The storage container 244 receives the material and a portion of the fluid used to flush the material from the containment chamber 216. The storage container 244 is then sealed to preserve the material for subsequent analysis as described in the applications incorporated by reference herein. Referring to FIGS. 31 and 32, the storage container 244 may include a valve or seal 252, such as a slit or duckbill valve, which permits introduction of part of the containment chamber 216 and seals the container 244 when the device is removed. The material in the container 244 may then be examined for any purpose such as to determine whether additional treatment is warranted.

The material may be stored in the container 244 using the fluid used to flush the material from the chamber 216. As shown in FIG. 32, the containment chamber 216 itself is used to open the seal by inserting the device through the seal 252. The material may be delivered directly into the storage container 244 from the device or may be delivered through a lumen, tube, intermediate chamber or the like on the material removal device or other device.

Figure 33:
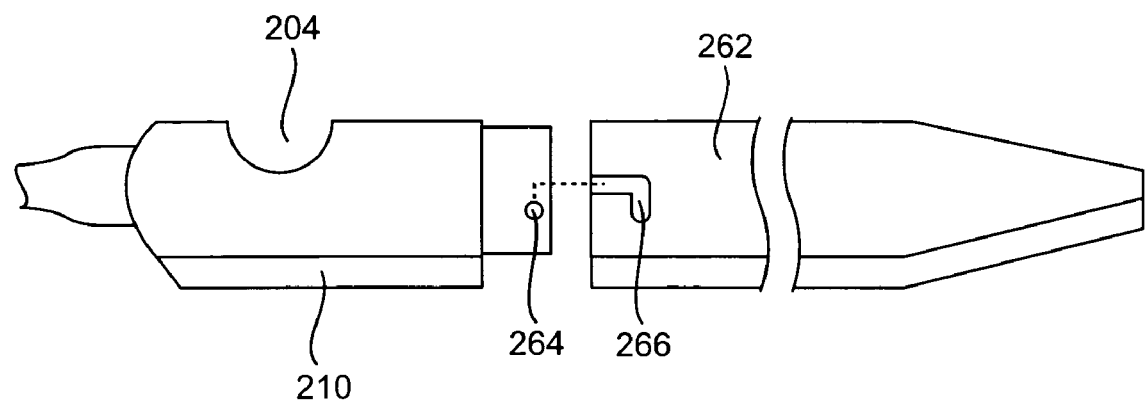
FIG. 33 shows a pin and slot attachment which permits removal of the containment chamber.
Figure 34:
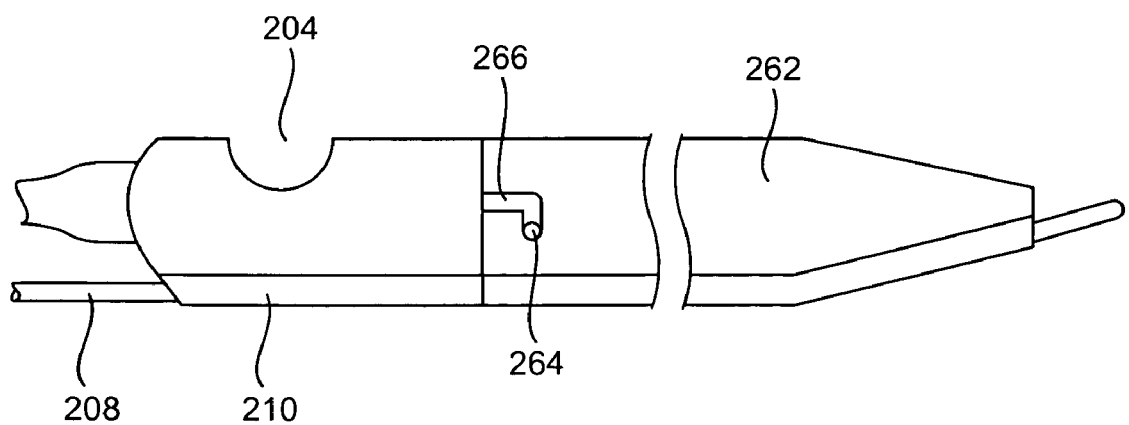
FIG. 34 show the containment chamber attached to the rest of the device and a guidewire positioned in the guidewire lumen to prevent removal of the containment chamber.

Referring now to FIGS. 23, 33 and 34, the device 200 may be designed so that the containment chamber 262 is removable. In particular, the present invention contemplates a system or kit including two or more removable containment chambers 216. One advantage of such a system is that the procedure time may be decreased compared to a device having only one containment chamber which must be cleaned before reintroducing the device into the patient. Depending upon the particular application, the containment chamber 262 might be filled and emptied a number of times. This requires the chamber 262 to be cleaned before being mounted again to the device for introduction into the patient. By providing two removable containment chambers 262 the user may remove the first containment chamber 262 when it is desired to remove the material contained therein and replace the first containment chamber 262 with the empty second containment chamber 262 and then reintroduce the device 200. The first containment chamber 262 may then be emptied while the user continues to remove material using the second containment chamber 262. For example, the pusher element 250 may be used to push material out of the chamber 262 (see FIGS. 35 and 36).

The containment chamber 262 has an interlocking pin 264 and slot 266 connection although any other suitable mechanism may be used. The pin 264 is advanced into the slot 266 and the containment chamber 262 is then rotated to align a section 268 of the guidewire lumen mounted to the containment chamber 262 with the rest of the guidewire lumen. The guidewire then acts to lock the containment chamber 262 and prevent detachment within the patient similar to other devices described herein.

Referring now to FIGS. 35 and 36, another atherectomy device 280 is shown which operates in essentially the same manner as the devices described above. The device 280 has a second opening 282 which is created by expanding or dilating a portion of the body. The second opening 282 may have any suitable structure which can be expanded such as a slit valve or duck bill valve. The second opening 282 is opened and the material is then removed by forcing the material out of one of the openings. The material may be forced through the second opening using the pusher element 250, a fluid in the manner described above, the cutting element 202 or any combination thereof. FIGS. 35 and 36 shows the pusher element 250 forcing material through the first opening 204, however, the pusher 250 may also be used to push material out of the second opening when introduced through the first opening 204 or through the exposed open end created when the containment chamber is removed as described above.

Referring to FIG. 23, another atherectomy device 200 is shown. Although the atherectomy device 200 may take on many different configurations, the atherectomy device 200 does have particular advantages over other devices as described herein and in applications and patents incorporated by reference. The catheter 200 may be constructed in any suitable manner including those methods described herein and in the patents and applications incorporated by reference.

The atherectomy device 200 has a rotating cutting element 202 which can move between the stored and working positions with a portion of the cutting element 202 becoming exposed through a first opening 204 when moving to the working position of FIG. 23. The device 200 is advanced through the blood vessel with the cutting element 202 in the working position so that material severed by the cutting element is directed through the first opening 204 and into a containment chamber 206. The device 200 is advanced over a guidewire 208 which extends through a guidewire lumen 210 on the device 200.

A distal portion 212 or tip of the device 200 may articulate or bend when the cutting element 202 moves from the stored position to the working position as described above and in the patents and applications incorporated by reference. Articulation or bending of the distal portion 212 tends to move the first opening 204 toward the wall of the blood vessel. The tip 212 may articulate in any suitable manner and various aspects of the present invention may be practiced with other features for moving the first opening 204 toward the wall of the blood vessel and orienting the cutting element 202 in an advantageous position without departing from the present invention.

The material cut by the cutting element 202 is directed through the first opening 204 and into a containment chamber 216 located distal to the first opening 204. The device 200 may be passed through the vessel a number of times with the material from each pass being stored in the containment chamber 216. As will be described below, material in the containment chamber 16 may be removed as desired and the device reintroduced a number of times to remove more material at the same or different locations.

Referring now to FIGS. 23-27, a second opening 218 may be created in the device 200 to help remove the material stored in the containment chamber 216. The device 200 may have a movable section 220 which is moved to expose or otherwise create the second opening 218. The movable portion 220 pivots or rotates to move between the closed position of FIG. 24 and open position of FIG. 26. For clarity, FIGS. 25 and 27 show the movable section 220 separated from the rest of the device 200 when oriented in the open and closed positions.

The movable section 220 may be located at the distal end of the containment chamber 216 near the distal tip of the device 200 opposite the first opening 204 although other locations may be used. The movable section 220 may have a curved section 222 which forms a ramp 224 to direct material out of the second opening 218 when in open position of FIG. 26. The bottom portion of the ramp 224 covers the second opening 218 when rotated into the closed position of FIG. 24. Of course, the second opening 218 may be created in any other manner without departing from various aspects of the present invention.

The guidewire lumen 210 extends along the device with a section 230 of the guidewire lumen 208 mounted to the movable section 220. In this manner, the movable section 220 may be locked by the guidewire 208. The guidewire 208 may lock the movable section 220 in another suitable way to prevent creation of the second opening 218 such as a locking element biased by the guidewire 208 when positioned in the guidewire lumen 210. When the device 200 is removed from the patient, the guidewire 208 is removed from the guidewire lumen 210 which permits rotation of the movable section to open the second opening 218.

Removal of the material from the containment chamber 216 is now described. The device 200 is removed from the patient and the guidewire 208 is removed from at least the section 230 of the guidewire lumen 210. The movable section 220 is then rotated to create the second opening 218.

Referring to FIGS. 28-30, the containment chamber 216 may then be mounted to a material removal device 236 which may include a storage container 244 to form a system or kit for removing material. The material removal device 236 has a throughhole 238 which forms a cavity 240 that receives the containment chamber 216. The device 200 has a first seal 242 and a second seal 243 which forms circumferential seals on both sides of the first opening 204 to isolate the first opening 204 from the second opening 218 except through the containment chamber 216. A fluid, either a gas or a liquid such as saline, is then delivered through the first opening 204 to force the material out of the second opening 218. The fluid may be delivered in any suitable manner such as with a syringe 220 or pump. The material removal device 236 may also form a seal around the second opening 218. For example, the containment chamber 216 may be introduced into a storage container 244 which has a seal 246 which isolates the second opening 218 as well. Although the first and second seals 242, 246 are shown as being independent they may also be formed by the same structure.

Once the second opening 218 has been created, material in the containment chamber 216 may be removed in a number of different ways. Referring to FIGS. 35 and 36, for example, a separate pusher 250 may be advanced into the containment chamber 216 to force material out of one of the openings 204, 218. The various methods may be combined, of course, to clear material from the containment chamber 216. For example, the cutting element 202 or a pusher element 250 (see FIGS. 35 and 36) may be used before, during or after use of the fluid to move the material from the containment chamber 216.

The material may simply be discarded in the appropriate manner after removal from the device. Alternatively, the material may also be saved in the storage container 244. The storage container 244 receives the material and a portion of the fluid used to flush the material from the containment chamber 216. The storage container 244 is then sealed to preserve the material for subsequent analysis as described in the applications incorporated by reference herein. Referring to FIGS. 31 and 32, the storage container 244 may include a valve or seal 252, such as a slit or duckbill valve, which permits introduction of part of the containment chamber 216 and seals the container 244 when the device is removed. The material in the container 244 may then be examined for any purpose such as to determine whether additional treatment is warranted.

The material may be stored in the container 244 using the fluid used to flush the material from the chamber 216. As shown in FIG. 32, the containment chamber 216 itself is used to open the seal 252 by inserting the device through the seal 252. The material may be delivered directly into the storage container 244 from the device or may be delivered through a lumen, tube, intermediate chamber or the like on the material removal device or other device.

Referring now to FIGS. 23, 31 and 32, the device 200 may be designed so that the containment chamber 262 is removable. In particular, the present invention contemplates a system or kit including two or more removable containment chambers 216. One advantage of such a system is that the procedure time may be decreased compared to a device having only one containment chamber which must be cleaned before being reintroduced into the patient. Depending upon the particular application, the containment chamber 262 might be filled five or more times. By providing two removable containment chambers 262 the user may replace a containment chamber 262 containing material with an empty containment chamber 262 and then reintroduce the device 200. The first containment chamber 262 may then be emptied by another person while the user continues to remove material which will now be held in the second containment chamber 262. For example, the pusher element 264 may be used to push material out of the chamber 262 from the second end out of the open end of the containment chamber 262.

The containment chamber 262 has an interlocking pin 264 and slot 266 connection although any other suitable mechanism may be used. The pin 264 is advanced into the slot 266 and the containment chamber 262 is then rotated to align a section 268 of the guidewire lumen mounted to the containment chamber 262 with the rest of the guidewire lumen. The guidewire then acts to lock the containment chamber 262 and prevent detachment within the patient similar to other devices described herein.

Referring now to FIGS. 35 and 36, another atherectomy device 280 is shown which operates in essentially the same manner as the devices described above. The device 280 has a second opening 282 which is created by expanding or dilating a portion of the body. The second opening 282 may have any suitable structure which can be expanded such as a slit valve or duck bill valve. The second opening 282 is opened and the material is then removed by forcing the material out of one of the openings. The material may be forced through the second opening 282 using the pusher element 250, a fluid in the manner described above, the cutting element 202 which would push the material out of the second opening 282 or any combination thereof. FIGS. 35 and 36 shows the pusher element 250 forcing material through the first opening 250 but the pusher 250 may also be used to push material out of the second opening when introduced through the first opening 204 or through the exposed open end created when the containment chamber is removed as described above.

While all the above is a complete description of the preferred embodiments of the inventions, various alternatives, modifications, and equivalents may be used. For example, while preferred cutters are moved proximally to move the cutter out of the cutting window, alternative embodiments may move the cutter distally to move the cutter out of the cutting window. Additionally, while most embodiments employ a cutter that extends out beyond the outer diameter of the cutting window, it may be possible to incorporate a cutter that stays within the diameter catheter body. Additionally, in some embodiments, the debulking assembly may be exposed through the window without causing a deflection of the distal portion of the catheter. Moreover, instead of having a distal tip that is rotatable relative to the proximal portion of the catheter, the catheter can include a shape memory material such that the catheter forms a jog or a pre-bent shape when it reaches its target area. Although the foregoing invention has been described in detail for purposes of clarity of understanding, it will be obvious that certain modifications may be practiced within the scope of the appended claims.

What is claimed is:

1. An atherectomy device for removing material from vascular location, comprising:
    an elongate body extending to a distal tip;
    a torque transmitting element contained within the elongate body, the torque transmitting element being rotatable;
    a first opening in the body;
    a cutting element coupled to the torque transmitting element, the cutting element being rotated by the torque transmitting element when cutting material from the vascular location, the cutting element being oriented to direct the material being cut from the vascular location through the first opening;
    a containment chamber formed along the body, the containment chamber receiving the material passing through the first opening which has been cut by the cutting element; and
    a second opening in the body, the second opening being selectively closed or opened by a user, the second opening being closed when the cutting element is used to cut material from the vascular location, the body being configured such that the second opening is prevented from being opened when the cutting element is used to cut material from the vascular location.

2. A method of removing material from the body lumen using an atherectomy device, comprising the steps of:
    providing an atherectomy device having an elongate body, a cutting element, a containment chamber, a first opening and a second opening, the body being configured such that the second opening is prevented from being opened when the cutting element is used to cut material from the body lumen, the containment chamber being positioned distal to the cutting element;
    cutting material from a body lumen using the cutting element, the cutting step being carried out by advancing the cutting element and the first opening through the body lumen, the material being cut by the cutting element passing through the first opening and into the containment chamber; and
    removing the material in the containment chamber by forcing the material through the second opening.

3. The method of claim 2, wherein the second opening is configured to be selectively opened or closed.

4. The method of claim 3, further comprising the step of:
    removing a guidewire from a guidewire lumen in the atherectomy device, wherein the guidewire prevents the second opening from being opened until removal of the guidewire from the guidewire lumen.

5. The method of claim 4, wherein:
    the providing step is carried out with the atherectomy device having a rotatable section, the rotatable section being rotated to selectively open the second opening, the guidewire preventing rotation of the rotatable section when the guidewire is positioned in the guidewire lumen.

6. The method of claim 5, wherein:
    the providing step is carried out with a portion of the guidewire lumen being coupled to the rotatable section.

7. The method of claim 6, wherein:
    the removing step is carried out using a fluid.

8. The method of claim 4, wherein:
    the providing step is carried out with the rotatable section having a ramp extending from a wall opposite the second opening to a distal portion of the second opening when the second opening is opened.

9. The method of claim 3, wherein:
    the second opening is configured to be selectively opened without detaching any part of the atherectomy device from the body.

10. The method of claim 2, wherein:
    the removing step is carried out by using fluid pressure to remove the material, wherein the fluid pressure is applied outside the body to force the material in the containment chamber out of the second opening.

11. The method of claim 2, wherein:
    the removing step is carried out by introducing a removing element through the first opening which forces the material out of the second opening.

12. The method of claim 2, further comprising the step of:
    changing the position of the cutting element so that part of the cutting element is exposed through the first opening during the cutting step.

13. The method of claim 2, wherein:
    the removing step is carried out with the atherectomy device being mounted to a removal device, the removal device applying the fluid pressure to the material so that the material leaves the containment chamber through the second opening.

14. The method of claim 13, wherein:
    the removing step is carried out with the removal device isolating the first opening from the second opening and applying the fluid pressure to the first opening so that material is forced out of the second opening.

15. The method of claim 2, wherein:
the removing step is carried out by directing the material into a storage container.

16. The method of claim 15, wherein:
the removing step is carried out with the storage container being attached to a material removal device.

17. The method of claim 15, wherein:
the removing step is carried out with the storage container being attached directly to the containment chamber.

18. The method of claim 2, wherein:
the providing step is carried out with the cutting element being movable to a position within the containment chamber to move material out of the second opening; and
the removing step is carried out by moving the cutting element into the containment chamber.

19. The method of claim 2, wherein:
the providing step is carried out with a pusher element which is removable from the atherectomy device, the pusher element being sized and configured to be introduced into at least one of the first and second openings to force material out of the other opening; and
the removing step is carried out by introducing the pusher element into at least one of the first and second openings and into the containment chamber to force the material out of the other opening.

20. A method of removing material from a vascular location, comprising the steps of:
coupling an atherectomy device to a removal device, the atherectomy device having a first opening, a second opening and a containment chamber in fluid communication with both the first and second openings, the atherectomy device having a cutting element which directs the material being cut through the first opening, the second opening being closed when the atherectomy device is being used to cut and remove material;
removing material from the vascular site using the atherectomy device, the material being directed through the first opening while the second opening remains closed;
opening the second opening after the removing step;
sealing around the first opening in the atherectomy device to isolate the first opening from fluid communication with the second opening except through the containment chamber; and
using a fluid to remove the material from the containment chamber, the fluid flowing into the containment chamber through the first opening and leaving the containment chamber through the second opening.

21. The method of claim 20, wherein:
the opening step is carried out by moving part of the device which forms part of the containment chamber.

22. The method of claim 21, wherein:
during the opening step the part of the device which is moved is not removed from the device.

23. The method of claim 21, wherein:
the opening step is carried out by rotating the part of the device relative to the rest of the device.

24. The method of claim 20, further comprising:
increasing fluid pressure at the first opening to force material out of the second opening.

25. The method of claim 20, wherein:
the flowing step is carried out by creating a pressure differential between the first and second openings to force material out of the second opening.

26. The method of claim 20, wherein:
the coupling step is carried out with the removal device having a cavity which receives the atherectomy device, the removal device sealing around an outer wall of the atherectomy device in a region between the first and second openings to fluidly isolate the first and second openings.

27. The method of claim 20, further comprising the step of:
directing the material which leaves the containment chamber into a material container, the material container having an interior which is fluidly coupled to the containment chamber; and
decoupling the material container from fluid communication with the containment chamber, the material container being used to store the material removed by the atherectomy device for analysis.

28. The method of claim 27, wherein:
the directing step is carried out with the material container being coupled to the removal device.

29. The method of claim 20, wherein:
the coupling and sealing steps are carried out with the first opening of the atherectomy device being used when introducing material which has been cut by the atherectomy device.

30. The method of claim 20, wherein:
the coupling and sealing steps are carried out with the second opening of the atherectomy device being opened after removing the device from the vascular location.

31. The method of claim 20, wherein:
the sealing step is carried out with a removal device having a cavity which receives the atherectomy device, the removal device forming a seal around the outer surface of the atherectomy device.

32. The method of claim 20, further comprising:
removing material from the containment chamber by delivering a pressurized fluid through the first opening.

33. The method of claim 20, wherein:
the removing step is carried out by moving the cutting element into the containment chamber, and wherein the method further comprises moving the cutting element to a position within the containment chamber to move material out of the second opening.

34. The method of claim 20, wherein:
the removing step is carried out by introducing a pusher element into at least one of the first and second openings and into the containment chamber to force the material out of the other opening, the pusher element being removable from the atherectomy device and being sized and configured to be introduced into at least one of the first and second openings to force material out of the other opening.

* * * * *